(12) United States Patent
Kraitzer et al.

(10) Patent No.: US 11,432,964 B2
(45) Date of Patent: Sep. 6, 2022

(54) EAR WAX REMOVAL DEVICE AND METHODS THEREOF

(71) Applicant: EARWAYS MEDICAL LTD., Rosh Ha'Ayin (IL)

(72) Inventors: Amir Kraitzer, Herzelia (IL); Miri Fahn, Tel Aviv (IL)

(73) Assignee: EARWAYS MEDICAL LTD., Rosh Ha'Ayin (IL)

( * ) Notice: Subject to any disclaimer, the term of this patent is extended or adjusted under 35 U.S.C. 154(b) by 169 days.

(21) Appl. No.: 16/202,591

(22) Filed: Nov. 28, 2018

(65) Prior Publication Data

US 2019/0091070 A1  Mar. 28, 2019

Related U.S. Application Data

(63) Continuation of application No. 15/100,824, filed as application No. PCT/IL2014/051049 on Dec. 3, 2014, now Pat. No. 10,238,545.

(60) Provisional application No. 62/015,556, filed on Jun. 23, 2014, provisional application No. 61/910,989, filed on Dec. 3, 2013.

(51) Int. Cl.
*A61F 11/00* (2022.01)
*A61M 31/00* (2006.01)

(52) U.S. Cl.
CPC .......... *A61F 11/006* (2013.01); *A61M 31/00* (2013.01)

(58) Field of Classification Search
CPC .............. A61B 17/32; A61B 17/32002; A61B 2017/320008; A61B 17/320758; A61B 17/1679; A61B 2017/00787; A61B 17/320708; A61F 11/00; A61F 11/002; A61F 11/004; A61F 11/006; A61F 9/0133; Y10T 408/898; Y10T 408/9097; Y10T 83/9394; A61M 5/3271

See application file for complete search history.

(56) References Cited

U.S. PATENT DOCUMENTS 3,422,186 A  1/1969 Sasmor
3,923,061 A  12/1975 Rossignol
(Continued)

FOREIGN PATENT DOCUMENTS

CN  2626465 Y  7/2004
CN  2693206    4/2005
(Continued)

OTHER PUBLICATIONS

"Earway TM PRO Tutorial", Earways Medical, Jun. 18, 2017, retrieved from the internet Aug. 23, 2018, https://www.youtube.com/watch?v=AlmzbJHPLvc.
(Continued)

*Primary Examiner* — Katherine M Shi
*Assistant Examiner* — Mikail A Mannan
(74) *Attorney, Agent, or Firm* — The Roy Gross Law Firm, LLC; Roy Gross

(57) ABSTRACT

A device for removing earwax from an ear canal includes a shaft; and an earwax collector head at an end of the shaft. The collector head is in the form of a helical strip surrounding a substantially elongated space. The helical strip has a cross section such that an outward facing surface of the helical strip is substantially flat and an interior surface of the helical strip radially tapers to an inward facing edge. A distal end of the helical strip tapers to present a wedge.

17 Claims, 19 Drawing Sheets

(56) References Cited

U.S. PATENT DOCUMENTS

| | | |
|---|---|---|
| 4,895,875 A | 1/1990 | Winston |
| 5,296,472 A | 3/1994 | Sanchez et al. |
| 5,380,711 A | 1/1995 | Sanchez et al. |
| 5,390,663 A | 2/1995 | Schaefer |
| 5,480,658 A | 1/1996 | Melman |
| 5,490,859 A | 2/1996 | Mische et al. |
| 5,820,319 A * | 10/1998 | Hull .................. B27G 15/00 408/214 |
| 5,888,199 A | 3/1999 | Karell et al. |
| 6,090,079 A * | 7/2000 | Fu .................. A61M 5/3271 604/192 |
| 6,152,940 A | 11/2000 | Carter |
| 6,155,987 A | 12/2000 | Scherl |
| 6,187,021 B1 | 2/2001 | Wim |
| 6,258,064 B1 | 7/2001 | Smith et al. |
| 6,264,664 B1 | 7/2001 | Avellanet |
| 6,406,484 B1 | 6/2002 | Lang |
| 6,417,179 B1 | 7/2002 | Burkhart et al. |
| 7,332,463 B2 | 2/2008 | Greenberg |
| 7,500,981 B1 | 3/2009 | Jubrail |
| 7,658,745 B2 | 2/2010 | Olson |
| 7,875,267 B2 | 1/2011 | Okajima et al. |
| 8,062,216 B2 | 11/2011 | Raghuprasad |
| 2003/0187469 A1 | 10/2003 | Olson |
| 2004/0126436 A1 | 7/2004 | Cagle et al. |
| 2006/0085018 A1 | 4/2006 | Clevenger |
| 2006/0156501 A1 | 7/2006 | Grunberger |
| 2006/0253087 A1 | 11/2006 | Vlodaver et al. |
| 2006/0287656 A1 | 12/2006 | Brown et al. |
| 2007/0009368 A1 | 1/2007 | Yang |
| 2008/0142385 A1 | 6/2008 | Stein et al. |
| 2008/0234602 A1 | 9/2008 | Oostman et al. |
| 2010/0082051 A1 | 4/2010 | Thorpe |
| 2010/0121363 A1 | 5/2010 | Huttner et al. |
| 2010/0137814 A1 | 6/2010 | Chew |
| 2010/0312198 A1 | 12/2010 | Guidi |
| 2011/0015489 A1 | 1/2011 | Raghuprasad |
| 2011/0017792 A1 | 1/2011 | Stull et al. |
| 2011/0066172 A1* | 3/2011 | Silverstein .............. A61F 13/38 606/162 |
| 2011/0071356 A1* | 3/2011 | Edwards ............ A61B 17/3421 600/142 |
| 2011/0166421 A1 | 7/2011 | Katiraei |
| 2012/0296355 A1* | 11/2012 | Burres .................. A61F 11/006 606/162 |
| 2013/0304103 A1 | 11/2013 | Burres |
| 2016/0302973 A1 | 10/2016 | Kraitzer et al. |
| 2016/0302974 A1 | 10/2016 | Chenal |

FOREIGN PATENT DOCUMENTS

| | | |
|---|---|---|
| CN | 2805725 | 8/2006 |
| CN | 201185988 Y | 1/2009 |
| CN | 201350157 | 11/2009 |
| CN | 101632612 A | 1/2010 |
| CN | 201426803 | 3/2010 |
| CN | 201481653 U | 5/2010 |
| CN | 201654722 U | 11/2010 |
| CN | 201719442 U | 1/2011 |
| CN | 201759743 U | 3/2011 |
| CN | 201894700 U | 7/2011 |
| CN | 202589763 U | 12/2012 |
| CN | 103006377 A | 4/2013 |
| DE | 20202497 U1 | 6/2002 |
| EP | 2412394 B1 | 2/2013 |
| FR | 2916135 A1 | 11/2008 |
| GB | 2520047 A | 5/2015 |
| JP | 3179742 B2 | 6/2001 |
| JP | 2011036605 A | 2/2011 |
| JP | 2011115346 A | 6/2011 |
| JP | 2011229610 A | 11/2011 |
| JP | 2012030028 A | 2/2012 |
| JP | 5410375 B2 | 2/2014 |
| KR | 20100052442 A | 5/2010 |
| KR | 20110017792 A | 2/2011 |
| KR | 20120066413 A | 6/2012 |
| WO | 2009063978 A1 | 5/2009 |
| WO | 2010017100 A1 | 2/2010 |
| WO | 2011085155 A2 | 7/2011 |
| WO | 2012023409 A1 | 2/2012 |
| WO | 2012158382 A1 | 11/2012 |

OTHER PUBLICATIONS

Notice of Reason for Refusal for Japanese Patent Application No. 2016-536901 dated Nov. 14, 2018, Japan Patent Office.

Notification Before Refusal dated May 22, 2018 for Israeli Patent Application No. 236240, issued from the Israel Patent Office.

The International Search Report and the Written Opinion for PCT/IB2018/051965, ISA/US, Alexandria, VA, dated Jul. 16, 2018.

The International Search Report and the Written Opinion for PCT/IL2014/051049, ISA/IL, Jerusalem, Israel; dated Apr. 22, 2015.

* cited by examiner

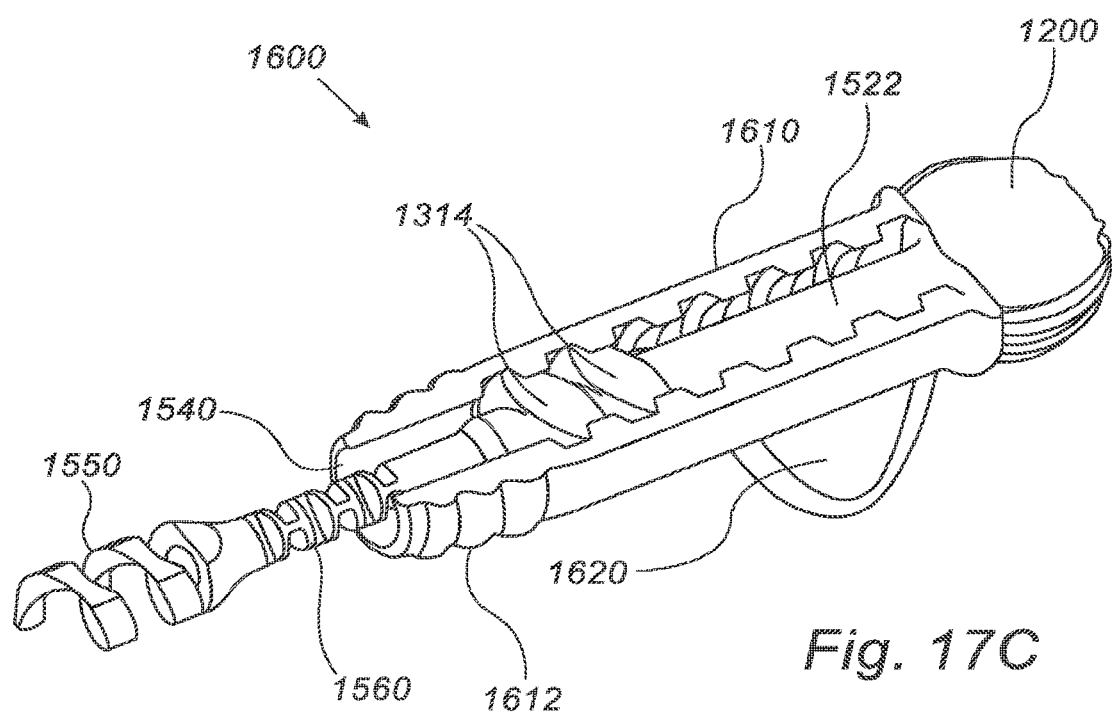

EAR WAX REMOVAL DEVICE AND METHODS THEREOF

FIELD OF THE INVENTION

The invention relates to an improvement for earwax removal or cerumen impaction relief.

BACKGROUND OF THE INVENTION

Earwax (cerumen) build-up and impaction in the external ear canal is a common problem faced by primary care physicians such as family practitioners, pediatricians and internists. Cerumen impaction is the presence of obstructing masses of earwax that block the ear canal. Cerumen accumulation can affect up to 6% of the general population and a much higher percentage of older people and people with cognitive impairment (e.g., and has been found to affect 57% of nursing home patients). In the US, cerumen accumulation leads to 12 million patient clinic visits and 8 million cerumen removal procedures annually.

In most cases of cerumen impaction, the removal is done by an Ear, Nose and Throat (ENT) doctor who usually removes the cerumen under vacuum, or using a curette, or by water irrigation using a syringe. Each approach is associated with risks and benefits. Using a curette allows a clinician to view the procedure and safely remove the cerumen while the lack of water lowers infection risk. However, using a curette requires considerable skill.

Irrigation or "syringing" is a standard method of earwax removal and approximately 150,000 ears are irrigated each week in the US. Irrigation, however, involves insertion of liquids using high pressure that might damage the eardrum (Tympanic membrane).

Ear care products for home use include wax softeners or Q-tips, which have very low effectiveness and sometimes involve safety issues. Softeners are often sufficient to treat mild cases of impacted cerumen, as well as reducing the need to be removed by a specialist in some cases. Wax softeners usually used to soften the wax in the ear are baby oil, glycerin, mineral oil, glycerol, olive oil, almond oil, hydrogen peroxide, docusate sodium (dioctyl sodium sulphosuccinate), dichlorobenzene, and carbamide peroxide. Hydrogen peroxide and 10% solution of sodium bicarbonate were found as effective means of removing or softening cerumen.

Current clinical practice for removing cerumen depends heavily on specialized clinicians such as ENT (ear, nose and throat) doctors. Home use products such as earwax softeners do not remove cerumen in the state of impaction but can be useful when used in conjunction with treatment by a ENT doctor or by a general practitioner (either by using irrigation, curette, vacuum, etc.).

Therefore, there is a long-felt need for a means and method for safe and mechanical removal of cerumen which can be carried out in its entirety without a clinician. Moreover, there is a need to simplify the procedure for general practitioners in order reduce the costs of and burden on ENT doctors.

SUMMARY OF THE INVENTION

There is thus provided, in accordance with an embodiment of the present invention, a device for removing earwax from an ear canal, the device including: a shaft; and an earwax collector head at an end of the shaft in the form of a helical strip surrounding a substantially elongated space, the helical strip having a cross section, such that an outward facing surface of the helical strip is substantially flat and an interior surface of the helical strip radially tapers to an inward facing edge, a distal end of the helical strip tapering to present a wedge.

Furthermore, in accordance with an embodiment of the present invention, the device is enclosed in a housing configured to enable the collector head to extend outward from the housing through an opening when the shaft is rotated.

Furthermore, in accordance with an embodiment of the present invention, the housing includes an inlet for connecting to a source of a cerumen dissolution agent.

Furthermore, in accordance with an embodiment of the present invention, the housing and the shaft include cooperating threading to extend of the collector head from the housing when the shaft is rotated.

Furthermore, in accordance with an embodiment of the present invention, the housing includes a stopper structure configured to restrict insertion of the housing into the ear canal.

Furthermore, in accordance with an embodiment of the present invention, the housing includes a restrictor that is shaped to engage an outer ear to constrain orientation of the housing relative to the ear canal.

Furthermore, in accordance with an embodiment of the present invention, the housing is configured to limit the outward extension of the collector head.

Furthermore, in accordance with an embodiment of the present invention, the shaft includes a knob limiting the outward extension of the collector head.

Furthermore, in accordance with an embodiment of the present invention, the housing includes a graspable fin.

Furthermore, in accordance with an embodiment of the present invention, the device includes a flexible section between the collector head and the shaft to enable the collector head to laterally bend relative to a longitudinal axis of the shaft.

Furthermore, in accordance with an embodiment of the present invention, the flexibility of the flexible section varies along the flexible section.

Furthermore, in accordance with an embodiment of the present invention, the flexible section includes a plurality of flexible segments.

Furthermore, in accordance with an embodiment of the present invention, the plurality of flexible segments includes alternating flexible segments that are bendable in mutually perpendicular lateral directions.

Furthermore, in accordance with an embodiment of the present invention, the wedge of the collector head is configured to yield to a bending force above a predetermined threshold.

Furthermore, in accordance with an embodiment of the present invention, the collector head includes a notch to enable yielding of the wedge.

There is further provided, in accordance with an embodiment of the present invention, a method for removing earwax from an ear canal, the method including: inserting into the ear canal a substantially helical collector head that is connected to a shaft; rotating the shaft to collect the earwax from the ear canal into the collector head; and removing the collector head from the ear canal.

Furthermore, in accordance with an embodiment of the present invention, inserting the collector head in to the ear canal includes placing a head opening of a housing that initially encloses the collector head on an exterior opening of the ear canal, and rotating a knob to rotate the shaft to extend the collector head out of the head opening and into the ear canal and to collect the earwax into the collector head.

Furthermore, in accordance with an embodiment of the present invention, the method includes introducing a cerumen dissolution agent into the ear canal.

Furthermore, in accordance with an embodiment of the present invention, introducing a cerumen dissolution agent includes connecting a body that initially encloses the collector head to a source of the cerumen dissolution agent.

Furthermore, in accordance with an embodiment of the present invention, the cerumen dissolution agent is introduced into the ear canal 1 minute to 20 minutes before inserting the collector head into the ear canal.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

FIGS. 5A-5D schematically illustrate softening of cerumen exposed to a cerumen softening liquid;

FIG. 17C is a sectional view showing internal components of the cerumen removal device shown in FIG. 17B;

DETAILED DESCRIPTION OF THE INVENTION

Figure 1:
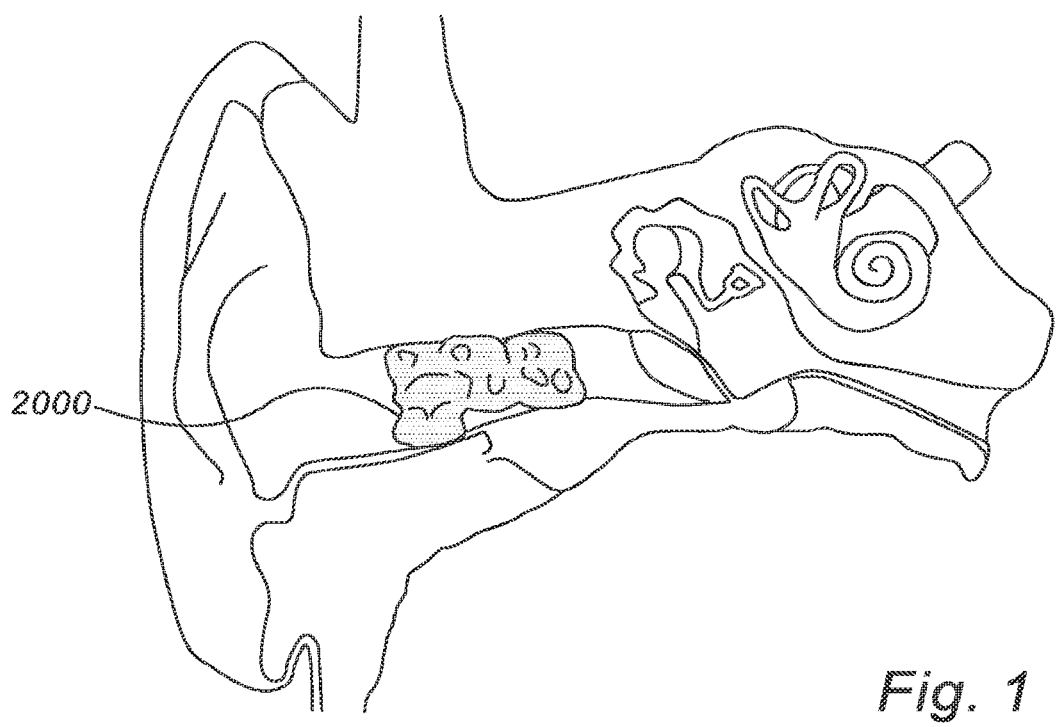
FIG. 1 illustrates the outer ear, showing impacted cerumen in the ear canal that is removable by an earwax removal device, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing." "computing." "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, us of the conjunction "or" as used herein is to be understood as inclusive (any or all of the stated options).

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for and method for providing mechanical removal of cerumen from the ear canal.

The term 'approximately' hereinafter refers to within 20% of the value.

The term 'plurality' hereinafter refers to any integer greater than one.

The term 'amass' hereinafter refers to accumulating or assembling a quantity of material.

The term 'distal' hereinafter refers to the part which, in use, is further into the external ear canal.

The term 'proximal' hereinafter refers to the part which, in use, is closer to the exterior of the ear. In a device comprising 2 parts, a first part resting against the external ear and a second part extending into the ear canal the proximal part is the first part and the distal part is the second part. The proximal end of the distal (second) part is that end of the distal part which is within the first (proximal) part.

The term 'hingedly connected' hereinafter refers to a connection which functions as a hinge, such that there exists at least one connecting part, each connecting part linking two connected parts, each connecting part being more flexible than the connected parts it joins, so that each connecting part functions as a hinge, allowing the adjoining connected parts to bend relative to each other in at least one direction.

The term 'main longitudinal axis' refers hereinafter to the axis extending along the long axis of the device. According to one embodiment, said device can be either a linear or a non linear device.

The term 'deform' refers hereinafter to any mechanical deformation e.g., bending, stretching, compression, twisting and any combination of these.

The term 'plastically deform' or 'plastic deformation' refers hereinafter to any permanent mechanical deformation.

The term 'braided basket' refers hereinafter to a plurality of fibers braided into a form which, when fully extended, resembles a basket. The action of the basket is to expand and collect cerumen during expansion and then capture it during contraction.

The term 'accordion pleat' refers hereinafter to substantially evenly spaced, substantially parallel folds. The accordion pleating can form, for non-limiting example, a series of parallel rows, or a helix.

The term 'outgoing soft cerumen' or 'soft cerumen' refers hereinafter to any form of cerumen mixture e.g., a paste, a wax, a liquid, or a semi-solid. Typically, the soft cerumen will have high viscosity.

The terms 'all three directions' and 'all three dimensions' refer hereinafter to three directions that form the axes of a three dimensional coordinate system. For non-limiting example, an object whose tip can bend in all three directions can be pointed at any desired point in space.

Cerumen is a naturally occurring substance that under normal conditions cleans, protects and lubricates the external auditory canal. Cerumen is eliminated by a self-cleaning mechanism which causes it to migrate out of the ear canal, assisted by jaw movement. Excessive earwax can harden in the ear canal and block the ear.

Cerumen is composed of sheets of corncocytes, originating from the deep and superficial external auditory canal, mixed with glandular secretions whereas keratin accounts for up to 60% of the cerumen plug phenotypes. In FIG. 1, a schematic of the ear canal is shown, containing impacted cerumen 2000.

Cerumen is a relatively hard material. In some cases, in order to simplify its removal, cerumen may be dissolved or wetted to so that it becomes soft and paste-like. In some embodiments, the current invention combines the effects of liquid immersion, cerumen soaking, and mechanical collection of the cerumen. In other embodiments, the cerumen is softened by other means, such as by a doctor syringing the ear, and the current invention mechanically collects the softened cerumen.

It should be pointed out that, while the cerumen softening fluids are low viscosity softening fluids, the outgoing softened cerumen, which could be in the form of a liquid, a paste or a wax, and which has high viscosity since it is a cerumen/softening fluid mixture.

The core concept behind embodiments of the present invention is to provide a simple mechanical device for cerumen removal.

According to some embodiments, the device may be useable by a person without medical training. According to other embodiments, the device is intended for use by healthcare professionals, such as physicians (e.g., general practitioners or ENT doctors). In some cases, the cerumen may be softened prior to use of the device. For example, a cerumen softening liquid, such as hydrogen peroxide or another liquid, may be introduced into the ear canal using a syringe or otherwise. In this case, after the cerumen has softened, the device may be used to remove the softened cerumen from the ear canal.

As introduced cerumen softening liquid may be left within the ear canal and in contact with the cerumen for a certain amount of time. In some cases, the liquid may contain medications in the form of a liquid, gel, powder, or foam (e.g., for topical treatment for a condition such as external otitis or mycosis).

Figure 2A:
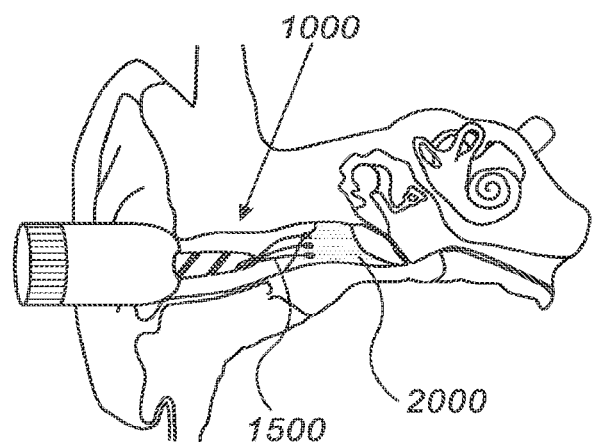
FIG. 2A schematically illustrates insertion of an earwax removal device in accordance with an embodiment of the present invention, into an ear canal with earwax and application of a cerumen softener.
Figure 2B:
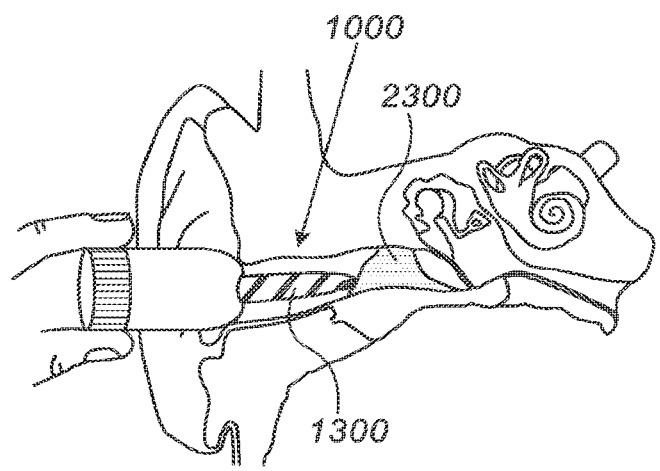
FIG. 2B schematically illustrates further insertion of the earwax removal device shown in FIG. 2A.
Figure 2C:
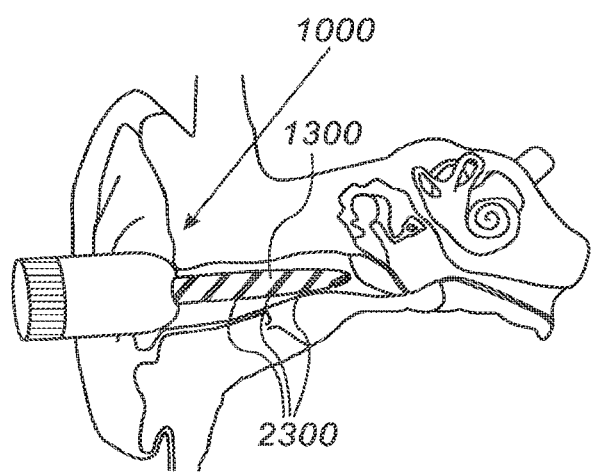
FIG. 2C schematically illustrates collection of the cerumen by the earwax removal device shown in FIG. 2B.

Cerumen removal treatment may be performed as illustrated by FIGS. 2A-2C:

FIG. 2A schematically illustrates insertion of an earwax removal device in accordance with an embodiment of the present invention, into an ear canal with earwax and application of a cerumen softener. Where cerumen dissolution is performed, with the device 1000 in the ear canal, fluid 1500 may exit the device 1000 and wet cerumen 2000. It should be noted that in some variants of the device, softening fluid may be introduced into the ear in any manner known in the art, e.g. via a syringe, before insertion of device 1000 into the ear.

Since hydrogen peroxide is a good cerumen softener and is often used in wax softeners, it may be used as the softening agent. In other cases, the softening agent may include baby oil, glycerin, mineral oil, glycerol, olive oil, almond oil, docusate sodium (dioctyl sodium sulphosuccinate), dichlorobenzene, carbamide peroxide, hydrogen peroxide, solution of sodium bicarbonate, commercial earwax removal liquid, another material, or any combination thereof.

FIG. 2B schematically illustrates further insertion of the earwax removal device shown in FIG. 2A. Collector head 1300 of device 1000 is introduced into the ear canal in order to mechanically collect cerumen. Collector head 1300 of the device 1000 may be operated to collect softened cerumen 2300 (or cerumen 2000 without softening).

FIG. 2C schematically illustrates collection of the cerumen by the earwax removal device shown in FIG. 2B. After the cerumen has been collected in the collector head 1300 of device 1000, device 1000, including collector head 1300 and the softened cerumen 2300 that is collected by collector head 1300 is removed from the ear canal.

The invention provides a single use, disposable product, designed, in some embodiments, for self-treatment by a patient at home. It can also be used, for non-limiting example, by a clinician or other caregiver treating a patient, in a clinical or residential setting. Non-limiting examples of treatment in a residential setting include a person treating himself or a parent treating a child. Other non-limiting examples include care of the physically frail (such as the elderly) or the physically or mentally disabled. Such care can be provided by the patient's family, by a caregiver, or by a physician. A non-limiting example of treatment in a clinical setting is use of the product by a doctor in the office as part of treatment.

In some embodiments, the overall process may take less than 20 minutes, in some cases less than 5 minutes or less than one minute.

The operation is quite simple; the device is inserted into the ear canal and rotational force is applied to a knob, the knob remaining on the exterior of the ear. The device is designed such that, when used properly, the user can not apply sufficient force in a longitudinal direction, inward along the ear canal to force the cerumen inward. Furthermore, the device is designed such that, when used properly, the user exerts a substantially rotational force to the knob, e.g. by rotating it at a constant speed.

Safety considerations: the maximal travel of the cerumen collecting mechanism is about 0.5-1.5 cm so that the maximal ear canal penetration is 1.5-2.5 cm from the external ear, leaving a safety distance of a minimum of 0.5-1 cm from the tympanic membrane. Furthermore, only moment forces can be exerted by the user, as opposed to forces that might push the device towards the tympanic membrane, thus significantly reducing the risk of tearing the membrane.

FIG. 3 illustrates the concept mechanism and its general action. The entire process is managed through an applicator 1000 that has several components:

A static mechanism 1100, referred to hereinafter as the "device body", that is lodged in the external ear canal and which, in preferred embodiments, includes a reservoir filled with about 0.2 ml to 3 ml of liquid. In preferred embodiments, the liquid is hydrogen peroxide 3%. Other possible liquids include, but are not limited to, other concentrations of hydrogen peroxide, oils such as mineral oil, baby oil or medicinal olive oil, sodium bicarbonate ear drops, and commercial ear drops such as, but not limited to, Earex™.

In some embodiments, the device does not include a reservoir of softening liquid. A softening liquid may be inserted into the ear by a physician or other clinician, in any manner known in the art, such as, but not limited to syringing. After insertion of the liquid and the passage of sufficient time for the liquid to soften the cerumen, the physician or other clinician inserts the device into the ear and operates it, thereby gently and reliably removing the softened cerumen from the ear.

In some embodiments, the reservoir of liquid is not within the main body of the device, but is within a container fluidly connected to the device and situated above the ear canal, for non-limiting example, at eye height, or resting above the ear between the upper portion of the pinna and the head, or on top of the head. In some of these embodiments, the reservoir can be held to the head by a ribbon tied around the head or by an elastic hand, or by any other means known in the art of holding objects in place on the head. In embodiments where the reservoir is above the ear canal, liquid flow into the ear canal is aided by the force of gravity.

In some embodiments, the reservoir of liquid is not associated with the device. In such embodiments, the liquid is introduced separately, preferably 1 minute to 20 minutes before insertion of the device into the ear, although longer or shorter times can be used, depending on the softening liquid being used and the hardness of the cerumen.

In some cases, no liquid is introduced into the ear canal.

A dynamic mechanism 1200, referred to hereinafter as the "knob", uses the rotational forces exerted by the user for powering the device throughout the treatment.

A mechanism (not shown) that wets the cerumen's 2000 front, comprising a reservoir of softening liquid (not shown), an orifice 1400 to deliver the liquid to the ear canal and a fluid connection (not shown) between the reservoir (not shown) in the device body 1000 and the orifice 1400.

A cerumen collector 1300 collects the cerumen 2000.

The applicator operates in the following manner: The applicator 1000 is inserted into the opening of the ear canal and the distal end 1500 of the static mechanism 1100 is lodged in the outer part of the ear. The user turns the knob 1200. This has two effects. The first is that the cerumen's front is wetted via the wetting mechanism (not shown) with a softening fluid such as, but not limited to, hydrogen peroxide. The wetting liquid is preferably delivered to the ear canal via the cerumen collector 1300 via at least one opening 1400 in the cerumen collector 1300. The second effect is that the knob 1200 imposes rotational maneuvers (curved arrow) that advance the collector 1300 in the direction (straight arrow) of the cerumen 2000. When the cerumen 2000 is soft, the collector head 1300 collects the soaked cerumen paste at the interface between the device and the hard cerumen. The tip of the cerumen collector 1300 does not progress into the ear canal if the cerumen is not soft enough. If the cerumen is too hard to be collected, the cerumen collector 1300 can collapse, it can rotate in place, or any other means known in the art can be used to prevent forward motion of the part of a collector head 1300 in contact with hard cerumen.

Figure 3A:
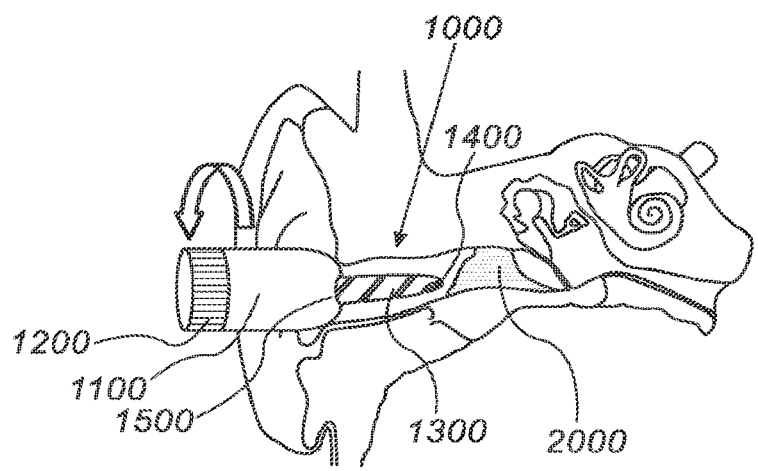
FIG. 3A schematically illustrates a process of using a device for removing cerumen from the ear.
Figure 3B:
FIGS. 3B-3D schematically illustrate a part of the device of FIG. 3A for insertion into the ear canal.
Figure 3C:
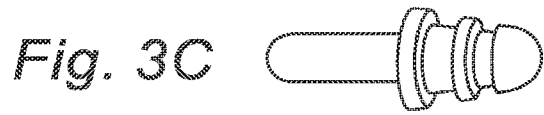
Figure 3D:
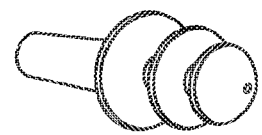

The distal end of the static mechanism, the nosepiece 1500, can be shaped like an earplug. Non-limiting examples of earplug shapes are shown in FIGS. 3B to 3D. The distal end of the earplugs, the end which extends furthest into the ear canal, is to the right in FIGS. 3B to 3D.

The knob 1200 includes a dynamic mechanism (not shown) that uses the rotational forces exerted by the user to power the device during treatment. In some embodiments, a wire or cable is connected to the static mechanism 1100, the wire or cable transmitting the rotational motion of the knob to the collector in order to mechanically clean the ear canal. The device constrains the user so that the only allowed maneuvers are those that impose rotational forces rather than compression forces so as to prevent the possibility of injury in the region of the tympanic membrane. The rotational force is used to both direct the collector into the inner part of the ear canal while rotating (i.e. a screw motion) as well as to transfer liquids to the cerumen's front through the orifice (not shown). A liquid may be introduced using another instrument such as a piston/syringe device before applying device 1000. It is possible, as a safety measure, that an element that prevents pushing the cerumen is added such that, when cerumen blocks the way or is still hard, the collector will remains in its position rather than be pushed in the direction of the tympanic membrane so as not to impose an unnecessary risk such as tearing the membrane.

In preferred embodiments, the knob mechanism includes a clutch or other decoupling mechanism such that, after the collector head has been extruded by a predetermined distance, preferably no more than 1 cm, further rotation of the knob produces no further extrusion of the collector head.

The cerumen collector head 1300 is configured to excavate and collect the cerumen, but not to push cerumen. The reason it cannot push cerumen into the ear canal is because it collector head 1300 has low longitudinal rigidity and is designed to collapse under a predetermined pressure that is less than the pressure required to push cerumen.

Furthermore, the collector head 1300 is designed to have low resistance to bending so as to facilitate its insertion into the inner part of the ear canal (note that the ear canal is tortuous in all three dimensions).

Embodiments for a mechanism for the collector head 1300 include, but are not limited to, a collector head comprised of soft material and shaped like a milling bit or Archimedes screw (diameter about 4 mm to 6 mm, length about 10 mm); a thin-walled hollow pipe with the ability to vary at least a portion of its cross sectional diameter to fit the diameter of the ear canal and the ability to vary the direction of portions of its longitudinal axis to follow the sigmoid shape of the ear canal; a thin-walled hollow pipe design having inner protrusions; a braided basket design; a sponge design, a scoop design and a shovel design. Other embodiments will be obvious to persons skilled in the art.

In embodiments with integral reservoir of cerumen-softening liquid, the reservoir can be within the collector, within the device body (static mechanism), and any combination thereof. In other embodiments comprising a reservoir, the reservoir can be fluidly connected to the device body, and be emplaced above the level of the device body (and the ear canal), such as on top of the ear between the pinna and the head, or at eye level or on top of the head. In the last two embodiments, the reservoir can be held in position by a ribbon or by an elastic band, or by any other means known in the art of holding objects in place on the head.

Figure 4A:
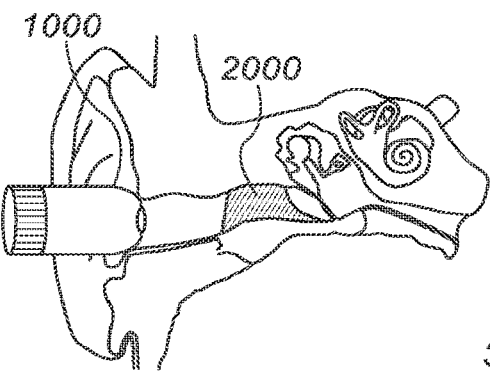
FIGS. 4A-4E schematically illustrate a process of using a device for removing cerumen from the ear.
Figure 4B:
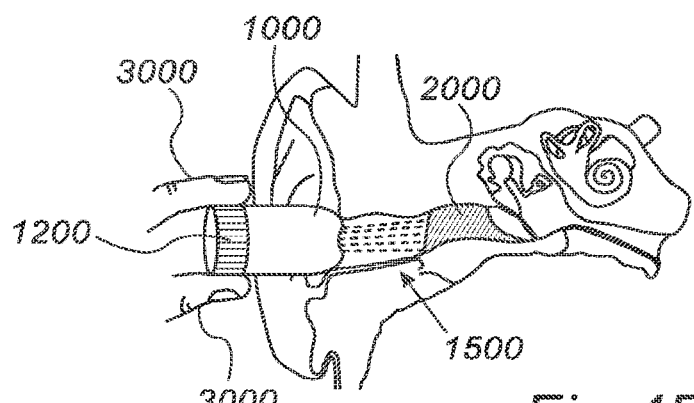
Figure 4C:
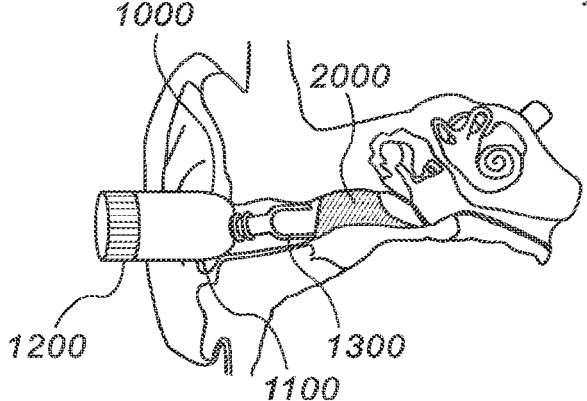
Figure 4D:
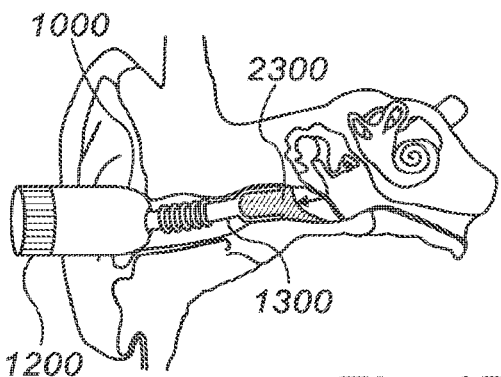
Figure 4E:
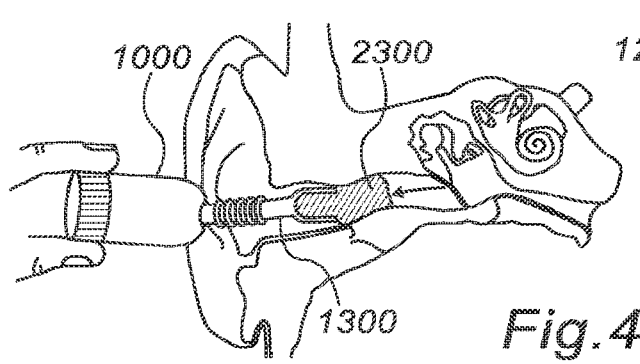

In an exemplary embodiment of the concept (FIGS. 4A-4E), a procedure for using the device is shown. In the first step (FIG. 4A), the device 1000 is inserted into the outer part of an ear canal contained impacted cerumen 2000.

In the second step (FIG. 4B), the knob 1200 of the device 1000 is turned (arrow) by a hand 3000. This induces flow of cerumen-softening liquid 1500 into the ear canal, where it contacts the cerumen 2000 and softens it.

In the third step (FIG. 4C), further rotation of the knob 1200 extrudes the collector head 1300 from the device body 1100, causing it to contact the cerumen 2000, which is now at least partly softened.

In the fourth step (FIG. 4D), the user continues to rotate the knob 1200, so that the collector head 1300 extends further from the device body 1100, thereby collecting the softened cerumen 2300.

The wetting process can be intermittent or continuous. In some embodiments, intended primarily for use by physicians or other clinicians, the cerumen is wetted and softened by the softening liquid separately, for example, by a syringe, before the device is inserted in the ear. In such embodiments, the device does not include a reservoir and operating the device includes collecting the softened cerumen and removing it from the ear canal.

In other embodiments, at the start of the process, all of the softening liquid is dispensed into the ear, after which the softened cerumen is collected and removed from the ear canal.

In yet other embodiments, the softening liquid is dispensed continuously, simultaneously with collection of the softened cerumen. In these embodiments, it is preferred that the dispensing of softening liquid begins before collection starts, so that, by the time the collector head reaches the cerumen, the cerumen has been softened and is collectable.

In still other embodiments, release of the softening liquid and operation of the collector are both intermittent. In these embodiments, softening liquid is released, after which the collector head collects the softened cerumen. Then further softening liquid is released, followed by collection of the softened cerumen. The steps of releasing softening liquid and collecting cerumen can be repeated a plurality of times. As a non-limiting example, (a) the softening liquid is dispensed for 2 rotations of the knob, followed by (b) 2 rotations of the knob during which there is neither dispensing of liquid nor rotation of the collector head. This is followed by (c) additional (e.g., 1 to 10) rotations of the knob during which the collector head collects softened cerumen. The process (a), (b), and (c) may be repeated several times. The device is then removed from the ear canal.

In the last step (FIG. 4E), the device 1000 is removed from the ear canal (arrow), with the softened cerumen 2300 being thereby removed from the ear canal, since it is held by the collector head 1300.

In some variants, the collector head 1300 is retracted into the device body 1100 during the removal step, in other embodiments (shown), the collector head 1300 is partially retracted into the device body 1100, in yet other variants, the collector head 1300 remains extended during removal of the device 1000 and the softened cerumen 2300 from the ear canal.

Any mechanism known in the art can be used to retract the collector head into the device body. Typical mechanisms include, but are not limited to, a wire or cable attached at one end to the collector head or to some portion of the distal end of the shaft, wherein, if a portion of the wire or cable is pulled, the collector head is withdrawn into the device body;

a collapsible or telescopic shaft that, when collapsed, pulls the collector head into the device body, a rotatable shaft that, when rotated, screws the collector head into the body, a direct coupling, e.g., to the knob or to a second knob, that, when the knob is rotated, the collector head retracts into the body, or any combination thereof.

FIGS. 5A-5D show the effects of cerumen softening liquid on a plug of hardened cerumen.

In FIG. 5A, cerumen plug 200 of hardened cerumen is shown lodged in tube 220. Tube 220 has been filled with softening liquid 210 above cerumen plug 200.

As shown in FIG. 5B, cerumen plug 200 at interface 230 has absorbed some of softening liquid 210. As a result, cerumen particles are suspended in softening liquid 210.

As shown in FIG. 5C, as the softening process continues, small fragments of the cerumen detach from cerumen plug 200 and become suspended in softening liquid 210, e.g., as visible inside oval 240.

Figure 5D:
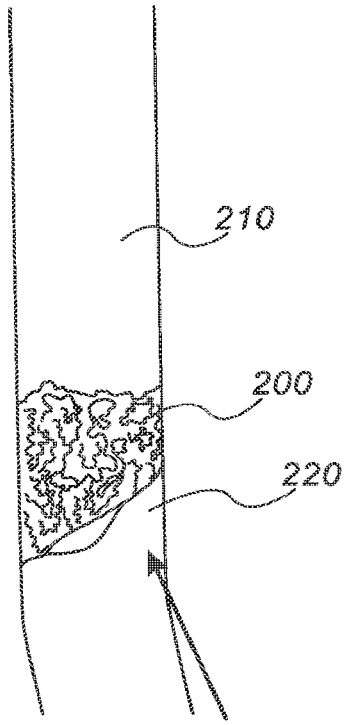
Figure 5D:
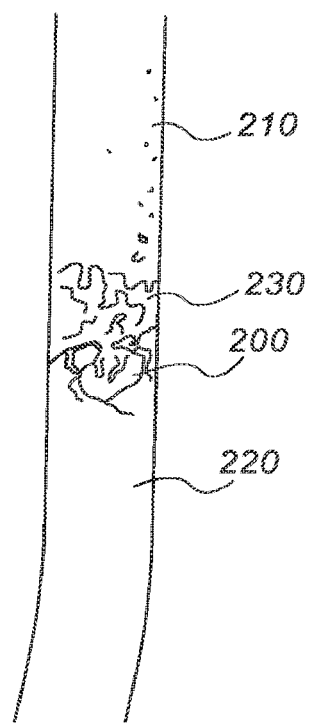
Figure 5D:
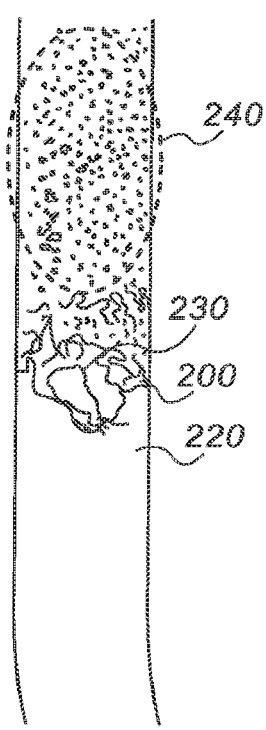
Figure 5D:
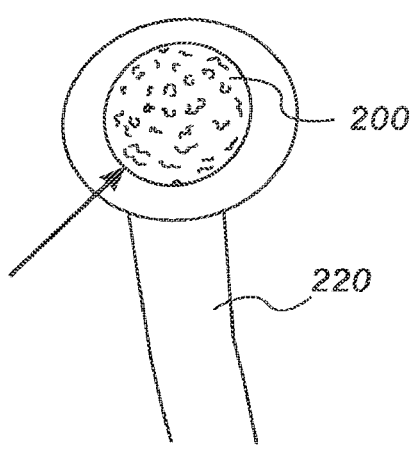

As shown in FIG. 5D, when the softening process is complete: the cerumen plug 200 has softened to soft paste with some cerumen particles, and floats at the top of tube 210.

In some embodiments, the device is inserted into the ear canal manually. In other embodiments, the device includes an insertion mechanism whereby, when the device is placed against the external ear, it is automatically inserted therein.

Devices with an automatic insertion mechanism and devices which operate automatically (such as, but not limited to, the device with biodegradable shell) are especially useful in the care of persons who, due to physical or mental infirmity, have difficulty inserting the device or for whom it is difficult for a physician or caregiver to insert the device.

Examples of embodiments of collector head designs are disclosed hereinafter.

Example 1

FIGS. 6A-6E illustrate an embodiment of the collector head in the form of an Archimedes screw with soft blades 1300. In this embodiment, the Archimedes screw is rotated by a rotational force applied to the collector head 1300 via the knob 1200 by the user. The blade tips 1312 remove the softened cerumen from the impacted mass; the removed cerumen then travels along the blades toward the outside of the ear canal. Note that the blades' soft and narrow design allows bending and thus the collector head fits the dimensions of the ear canal at different depths within the canal (note that the ear canal is not homogenous in its diameter along its length, and also differs from ear to ear and person to person).

Figure 6A:
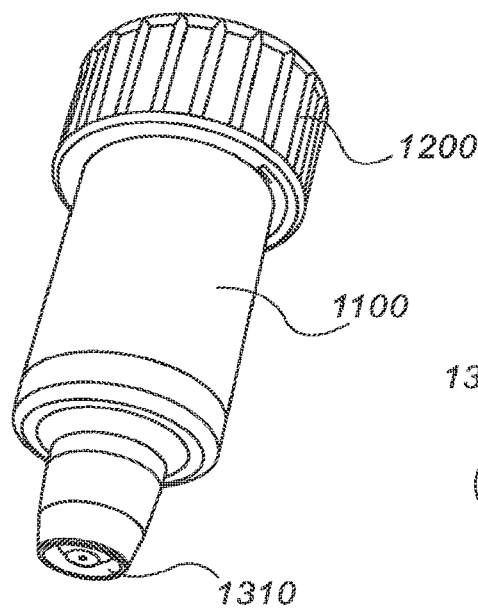
FIGS. 6A-6E schematically illustrate an embodiment of the device.

FIG. 6A illustrates the Archimedes screw design with the screw 1310 at its innermost position (within the device body).

Figure 6B:
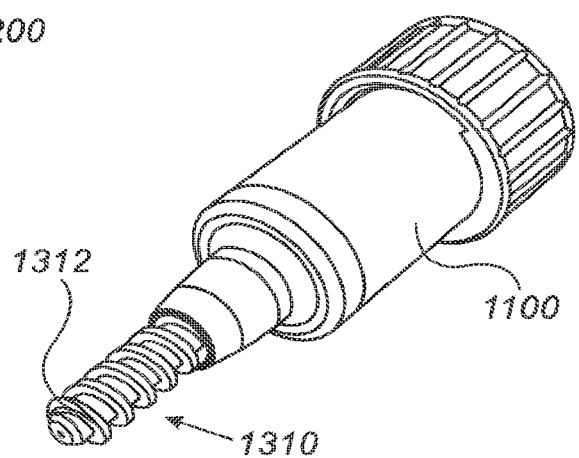

FIG. 6B illustrates the Archimedes screw design with the screw 1310 at an extended position, showing the screw 1310 and the blade tips 1312.

Figure 6C:
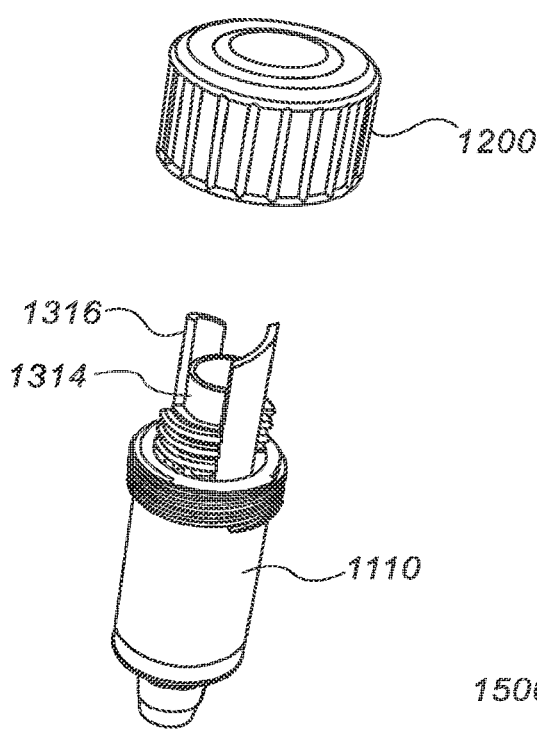

FIG. 6C illustrates the Archimedes screw design partially disassembled, with the knob 1200 removed, showing the extruding mechanism 1314 for the Archimedes screw and the device body 1100. A clutch-like mechanism 1316 disconnects the motion between knob 1200 and the extruding mechanism 1314 when the extruding mechanism is displaced about 1 cm. The extruding mechanism 1314 is connected to the Archimedes screw 1310 so that its disconnection is required so as prevent it from advancing further in the direction of tympanic membrane, although the user may continue to turn the knob 1200. The clutch mechanism ensures that, although the Archimedes screw continues to turn, it cannot advance further.

Figure 6D:
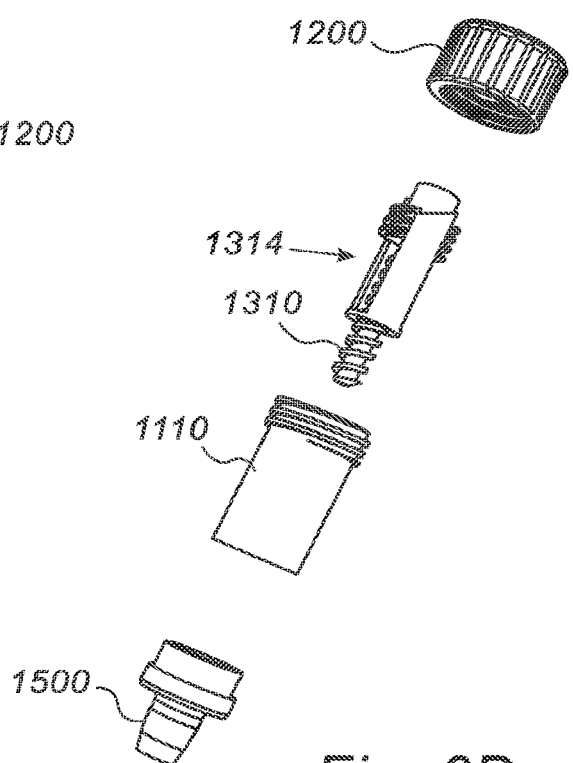

FIG. 6D illustrates an exploded view of the Archimedes screw design. The exploded view shows the knob 1200, the extruding mechanism 1314 for the Archimedes screw 1310, the outer housing 1100 for the device, the clutch-like mechanism 1316, and the nosepiece 1500 which fits into the outer ear and from which the Archimedes screw 1310 will protrude. Container 1110 may be filled with a cerumen dissolution agent (e.g., hydrogen peroxide or another fluid) that may be dispensed into the ear canal.

Figure 6E:
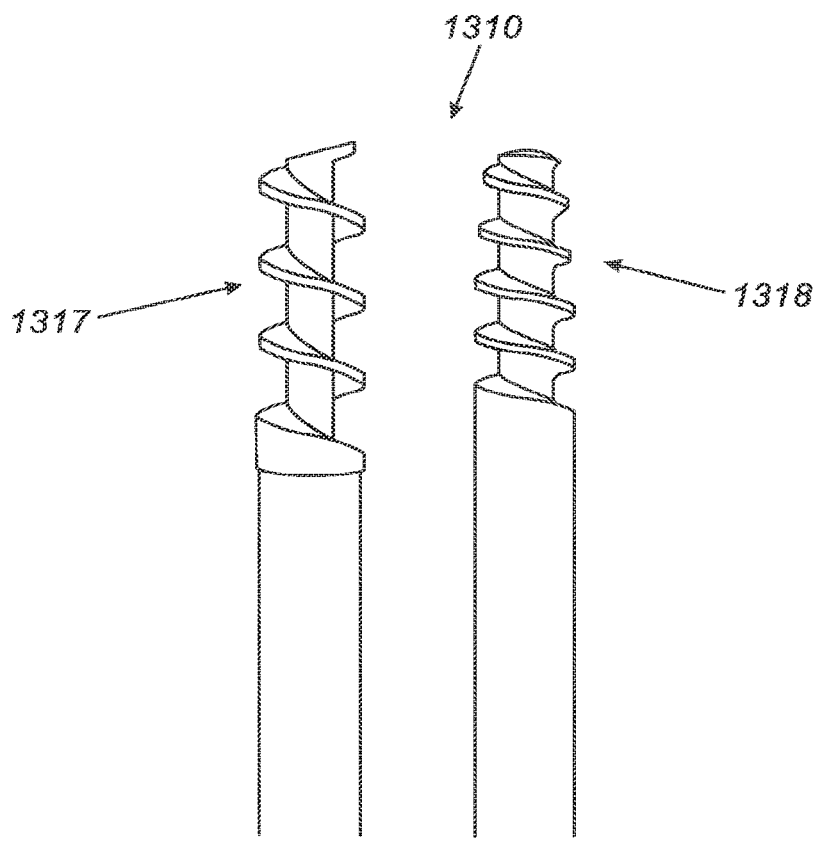

FIG. 6E illustrates two different Archimedes screw 1310 designs. The left Archimedes screw 1317 has a coarse pitch, while the right Archimedes screw 1318 has a fine pitch.

The Archimedes screw 1310 can be composed of soft materials such as, for non-limiting example, silicone, fiber mesh, cellulose, polyurethane, high density or low density polyethylene, polyamide, polypropylene, and any combination thereof.

The Archimedes screw 1310 can include a single piece, or it can include a plurality of segments connected by a flexible section, said flexible section comprising accordion pleating, a helical spring or a hinging means, the flexible section allowing the Archimedes screw 1310 to deform to follow the tortuosity of the ear canal. The hinging means can include a hinging mechanism, or it can include a shaft comprising a plurality of hinging sections, as described hereinafter.

The flexible section, by enabling bending in all three dimensions, prevents resistance of the collector head to bending, especially about its longitudinal axis and ensures that the Archimedes screw conforms to the tortuosity of the ear canal.

Example 2

Figure 7:
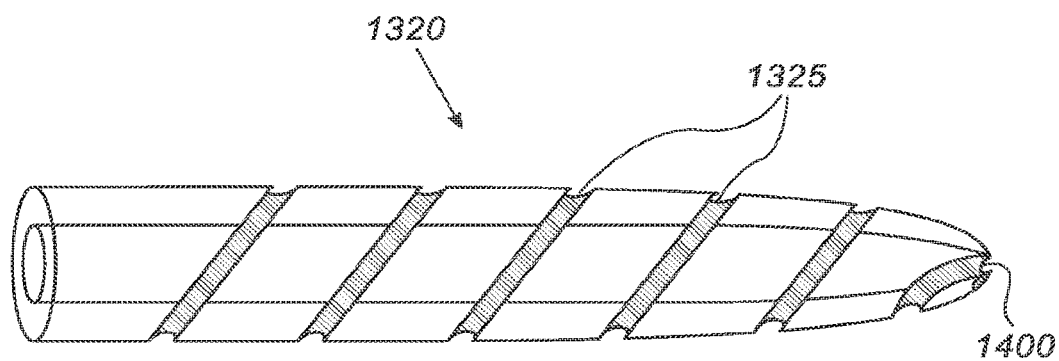
FIG. 7 schematically illustrates a collector head in the form of a milling bit, in a accordance with an embodiment of the present invention.

FIG. 7 discloses an embodiment of the collector head in the form of a milling bit 1320 composed of soft materials, for non-limiting example, silicone, fiber mesh, etc. In the bit design, cerumen is wetted by fluid supplied from a reservoir (not shown) through an inner pipe (not shown) and orifice 1400. Cerumen is collected within the bit's grooves 1325 as the bit is rotated within the ear canal.

The milling bit 1320 can be composed of soft materials such as, for non-limiting example, silicone, fiber mesh, cellulose, polyurethane, polyethylene, polyamide, polypropylene, and any combination thereof.

The milling bit 1320 can include a single piece, or it can include a plurality of segments connected by a flexible section, said flexible section comprising accordion pleating, a helical spring or a hinging means, the flexible section allowing the milling bit 1320 to deform to follow the tortuosity of the ear canal. The hinging means can include a hinging mechanism, or it can include a shaft comprising a plurality of hinging sections, as described hereinafter.

The flexible section, by enabling bending in all three dimensions, prevents resistance of the collector head to bending, especially about its longitudinal axis and ensures that the milling bit conforms to the tortuosity of the ear canal.

Example 3

FIGS. 8A-8D disclose an embodiment of the collector head formed as a plurality of fibers braided into a form which, when fully extended, resembles a basket. This embodiment will be referred to hereinafter as the "braided basket" collector device 1340. In the braided basket design, the braiding forms a hollow, preferably closed-ended pipe composed of elastic fibers. The braiding facilitates the expansion of the braided basket to match the dimensions of the ear canal at any location within the ear canal. With this design, the basket 1346 is in its minimal diameter mode when it is retracted and at least substantially inside a sleeve 1343 and it opens to an expanded position when extended at least partly outside the sleeve 1343. In its open state, the basket 1346 captures the cerumen and, when the sleeve 1343 covers the basket 1346 entirely or partially, it reduces the diameter of the basket 1346 and thereby collects the cerumen within the bore of the braided basket 1346.

In use, the device is inserted into the ear canal with the braided basket 1346 in its retracted position. A knob or handle may be rotated, or another mechanism operated, to extend braided basket 1346 out of sleeve 1343 and to rotate braided basket 1346. Rotation of the braided basket 1346 collects the softened cerumen within the basket. When the device is to be removed from the ear canal, the braided basket 1346 is retracted into the sleeve 1343, thereby trapping the cerumen inside the collector device 1340 and ensuring its removal from the ear canal.

The fibers comprising the basket can be of any sufficiently stiff, sufficiently elastic material. Fiber materials may include, but are not limited to, a metal (e.g., steel, nickel-titanium, beta-titanium, or another metal), plastic, natural fibers, polyester, rayon, nylon, woven material non-woven material, another material, or any combination thereof. The material can be monofilament i.e., comprising a single fiber, or multifilament, comprising a plurality of fibers.

Multifilament fibers can include filaments wound around each other without a core, filaments wound around a core, filaments braided together, and any combination thereof. The filaments can be identical or can differ. For example, the core can include a filaments thicker or of a stiffer material than the wrapping filaments.

The fibers can be coated. Each filament of a multifilament fiber can be individually coated, or the fiber itself can be coated.

Coatings can improve, among other factors, stiffness, breaking strength, flexibility, slidability of the fibers against each other (non-stick coatings), and biocompatibility.

Fiber coatings can include, but are not limited to, metal, plastic, Teflon, natural fibers, polyester, rayon, nylon, polyurethane, hydrogel, hydrophilic coating, woven material, non-woven material and any combination thereof.

Figure 8A:
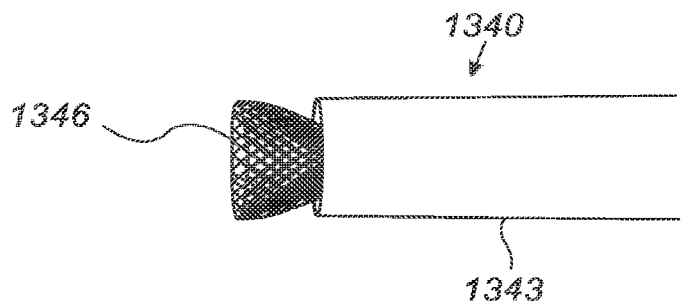
FIG. 8A schematically illustrates a collector head in the form of a braided basket design in a retracted position, in accordance with an embodiment of the present invention.

FIG. 8A shows an embodiment of a braided basket design in a retracted position. Part of the braided basket 1346 is visible at the end of the sleeve 1343.

Figure 8B:
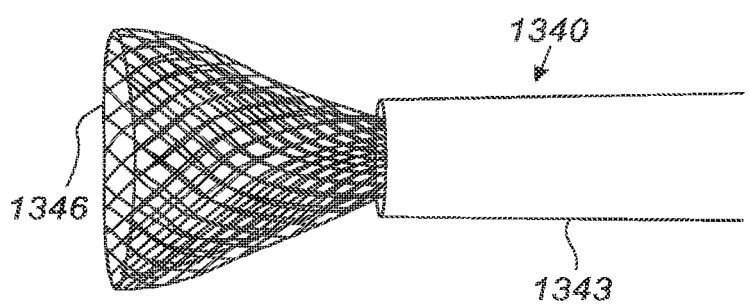
FIG. 8B schematically illustrates the collector head of FIG. 8A when partially extended.

FIG. 8B shows an embodiment of the braided basket design when partially extended. The braided basket 1346 is clearly visible at the end of the sleeve 1343 and has expanded so that it is significantly wider than the sleeve 1343.

Figure 8C:
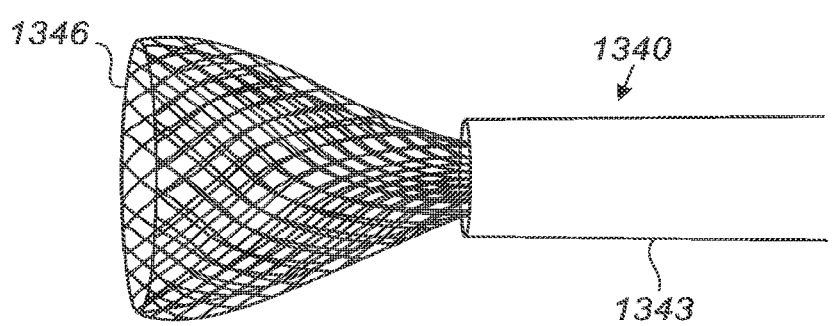
FIG. 8C schematically illustrates the collector head of FIG. 8A when mostly extended.

FIG. 8C shows an embodiment of the braided basket design when mostly extended. The braided basket 1346 is wider than when slightly extended and extends further from the end of the sleeve 1343.

Figure 8D:
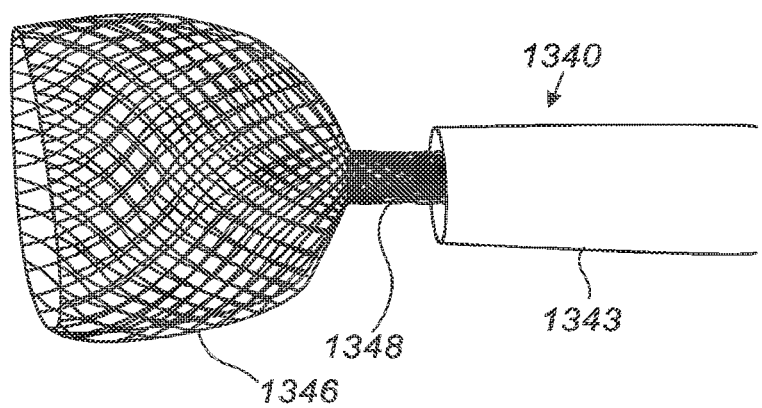
FIG. 8D schematically illustrates the collector head of FIG. 8A when fully extended.

FIG. 8D shows an embodiment of the braided basket design when in a fully extended state. The shaft 1348 holding the braided basket 1346 can be clearly seen, and the braided basket 1346 is now basket-shaped rather than the more conical shape seen in FIGS. 8A-8C.

It is clear that fluid can easily pass from the hollow sleeve and through the braiding of the basket to reach the cerumen.

Example 4

Figure 9A:
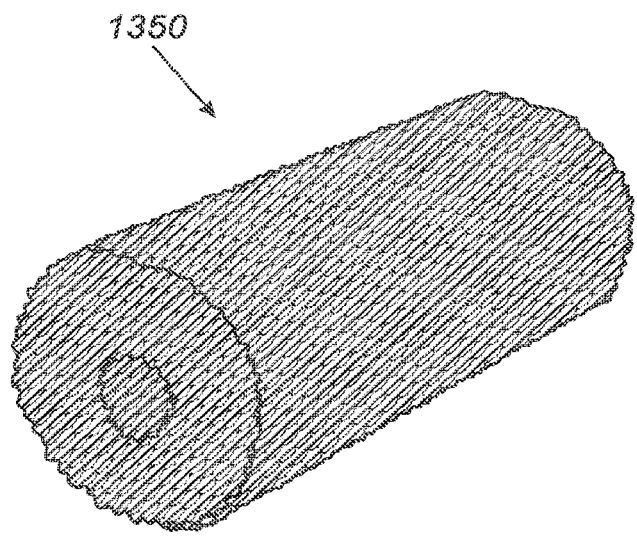
FIG. 9A schematically illustrates a collector head in the form of a sponge, in accordance with an embodiment of the present invention.

FIG. 9A illustrates an embodiment of the collector head formed of a sponge 1350. In this design, the collector head is of a substantially cylindrical shape and is formed of a spongy material. The sponge is kept wet by the fluid from the reservoir; the fluid flows through the sponge and wets portions of the cerumen's front. Rotation of the sponge causes collection of the softened cerumen within the pores of the sponge. The sponge is elastic so that it can deform to fit the size and shape of the external ear canal.

The sponge can be formed in other shapes such as, but not limited to, a cone or the frustum of a cone.

The sponge can be mounted directly to the knob or can be connected to the knob via a shaft or sleeve or other connecting mechanisms as is known in the art. One embodiment of such a shaft is described hereinafter.

The sponge can be comprised of materials including, but not limited to, cellulose, polyurethane, polyamide, polypropylene, polyethylene, and any combination thereof.

Figure 9B:
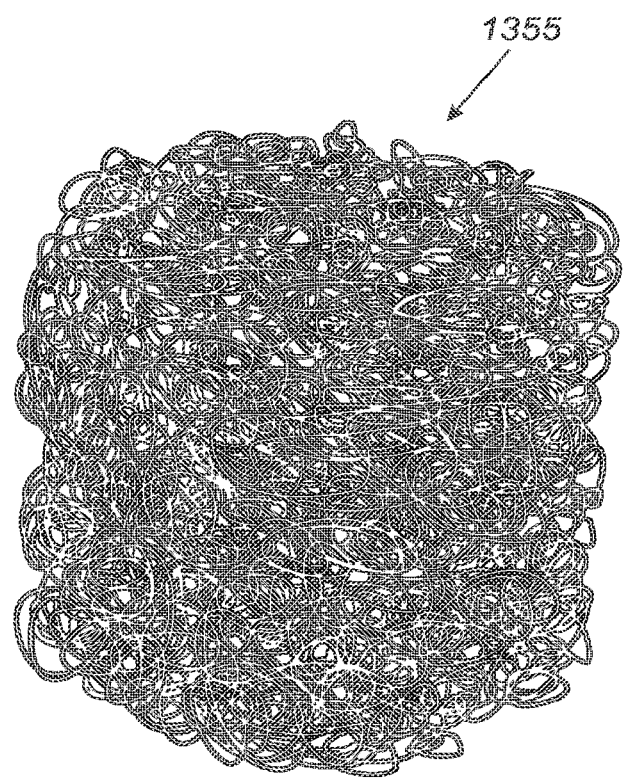
FIG. 9B schematically illustrates a collector head in the form of a fiber sponge, in accordance with an embodiment of the present invention.

FIG. 9B illustrates another embodiment 1355, in which the sponge is composed of fine fiber twisted, crumpled, bent or braided so as to form a body composed of fiber. The exemplary embodiment of FIG. 9B is formed of fiber bent into the form of a cylinder; the fiber body can be formed in other shapes such as, but not limited to, a cone or the frustum of a cone.

It should be pointed out that, while the cerumen softening fluids are low-viscosity softening fluids, the outgoing soft cerumen, which could be in the form of a liquid, a paste or a wax, has high viscosity since it is a cerumen/softening-fluid mixture.

Example 5

Figure 10A:
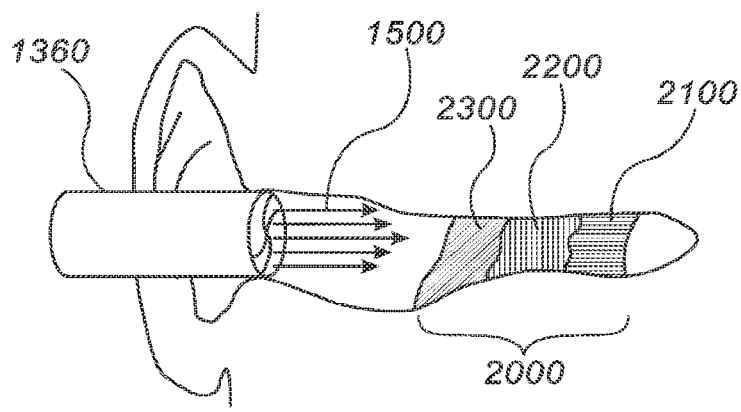
FIG. 10A schematically illustrates insertion into an ear canal of a collector head in the form of a hollow pipe, in accordance with an embodiment of the present invention.
Figure 10B:
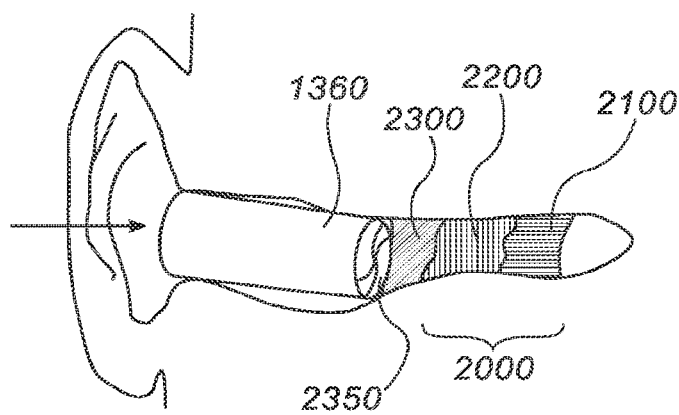
FIG. 10B illustrates further insertion of the collector had of FIG. 10A.
Figure 10C:
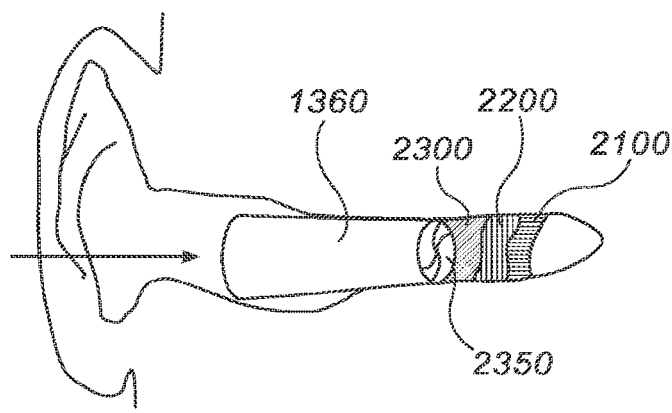
FIG. 10C schematically illustrates insertion of the collector head of FIG. 10B to collect cerumen.

FIGS. 10A-10C illustrate a method of using a collector head in the form of a hollow pipe 1360. With the hollow pipe design, as the leading (distal) edge of the pipe advances inward toward the eardrum, a new front of cerumen 2000 is wetted and is collected by the cerumen collector. This process is repeated constantly until the ear canal is cleared.

The hollow pipe is composed of a very thin elastic foil. The elastic foil is folded around and is made of sufficiently elastic spring-like material so that it has radial elastic forces (similarly to a watch spring) towards the ear canal walls in order to increase or reduce its diameter according to its location within a tunnel such as the ear canal. The rationale is that the elastic foil is spring-like enough that it is pressed against the walls of the ear canal. This, along with the thinness of the foil, ensures that the elastic foil collector head passes between the cerumen in the car canal and the walls of the ear canal, so that the cerumen is surrounded by the foil collector head and collected within it. Furthermore, the radial forces ensuring that the elastic foil is pressed against the walls of the ear canal prevent the foil collector head from pushing the cerumen deeper into the ear canal.

FIGS. 10A-10C show the functioning of the hollow pipe design. Liquid 1500 exiting the pipe 1360 wets the cerumen 2000 and softens it, producing fully wetted cerumen 2300 and, further from the pipe opening, partially wetted cerumen 2200, while unwetted cerumen 2100 remains in the regions furthest from the pipe.

FIG. 10A illustrates the situation at the start of the process. At this point, the pipe 1360 has not reached the cerumen 2000, although the wetting fluid 1500 has, producing partly wetted cerumen 2200 and fully wetted cerumen 2300, although some of the cerumen 2100 is still unwetted.

FIG. 10B illustrates the situation after the pipe 1360, moving inward (arrow), has reached the cerumen 2000. Some of the fully-wetted cerumen 2350 has been collected inside the pipe and the wetting fluid (not shown) is softening additional portions of the cerumen plug 2200. The amount of unwetted cerumen 2100 has decreased.

As the process continues (FIG. 10C), the pipe 1360 continues to move inward toward the base of the external ear canal (arrow) and to collect the wetted cerumen within it 2350. Near the end of the process, as shown in FIG. 10C, most of the wetted cerumen 2300 has been collected; only small amounts of partially wetted 2200 and unwetted cerumen 2100 remain.

Figure 11A:
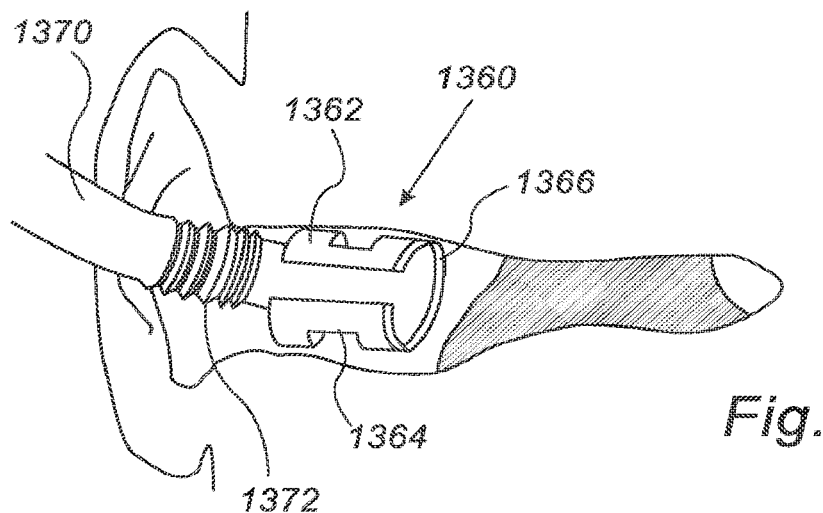
FIG. 11A schematically illustrates a thin hollow pipe collector, in accordance with an embodiment of the present invention, when initially inserted into an ear canal.
Figure 11B:
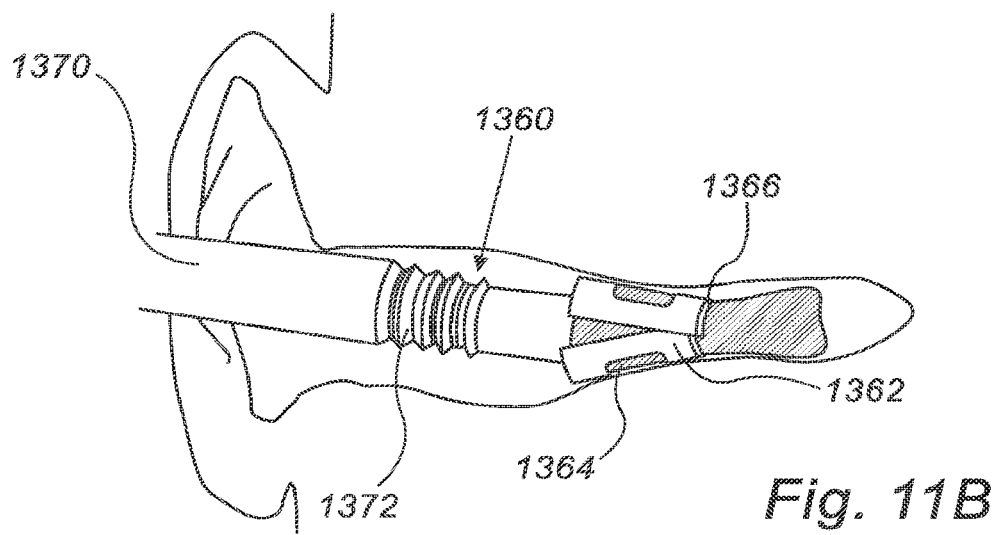
FIG. 11B schematically illustrates further insertion of the thin hollow pipe collector of FIG. 11A into the ear canal and collection of cerumen.
Figure 11C:
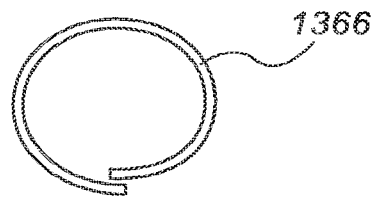
FIG. 11C schematically illustrates a deformable ring of the thin hollow pipe collector shown in FIG. 11A.

FIGS. 11A-11C illustrate another embodiment of a hollow pipe design, comprised of a very thin (in the range of 0.05 mm thick to 0.5 mm thick, preferably approximately 0.1 mm thick) elastic foil. The elastic foil is made of a spring-like material and is folded around so there exist in it radial elastic forces which enable it to increase or decrease its diameter in order to conform to the shape of the walls of the ear canal. The rationale is that the elastic foil is spring-like enough that the elastic foil is pressed against the walls of the ear canal. This, along with the thinness of the foil, ensures that the elastic foil collector head passes between the cerumen in the ear canal and the walls of the car canal, so that the cerumen is surrounded by the foil collector head and collected within it. Furthermore, the radial forces that ensure that the elastic foil is pressed against the walls of the ear canal may prevent the foil collector head from pushing the cerumen deeper into the ear canal and may ensure that the foil is opened to as large a diameter as possible at each cross-section along the ear canal.

Because the diameters of the collector leading (distal) edge, ear canal and cerumen plug are approximately the same, the collector can encompass the cerumen and, because of the thinness of the material of the thin hollow pipe, the collector can advance between the cerumen and the wall of the ear canal. As the collector advances, its diameter, and especially the diameter of its leading portion, is reduced since the diameter of the ear canal is decreasing.

At some point, some portion of the leading (distal) portion of the collector will undergo plastic deformation. Having undergone plastic deformation, the leading (distal) portion of the collector will remain in approximately its final, deformed shape and will not regain its original expanded shape upon removal from the ear, thereby ensuring retention of the cerumen within the collector.

In some embodiments, the elastic foil material does not undergo plastic deformation. In these embodiments, the collector includes a ring, preferably a metal ring (hereinafter referred to as the 'deformable ring'), approximately at the collector's leading (distal) edge, which undergoes the appropriate plastic deformation when the foil collector head is approximately at its furthest depth within the ear canal.

In preferred embodiments, the collector, at the end of treatment, has been reshaped into a substantially conical shape and, therefore, a substantially closed-sided and closed-ended shape so that, when the device is removed from the ear, the collector retains the captured cerumen.

Since the cerumen is efficiently collected within the foil, removal of the device from the ear also removes the cerumen therefrom. The plastic deformation of the deformable ring by the ear canal, by tending to close the opening at the distal end of the foil collector head, increases the efficiency of removal of the cerumen from the ear.

In some embodiments, the foil collector head further includes a deformable ring at its proximal end; in these embodiments, the foil collector head includes deformable rings at both the distal and the proximal ends.

The pipe can be composed of any material capable of forming a very thin, highly elastic foil. In some embodiments, the foil is comprised of polyimide. Other foil materials include polyvinyl chloride (PVC), polyether ether ketone (PEEK), polyethylene, polypropylene, polyamide and laminates of thermoplastic elastomer and thermoplastic plastics. Any material capable of forming a very thin, highly elastic, foil (between 0.05 mm thick and 0.5 mm thick, preferably approximately 0.1 mm thick) known in the art can be used. The foil can, optionally, also be stiffened with struts or other stiffening mechanisms known in the art.

FIG. 11A schematically illustrates a perspective view of an embodiment of a thin hollow pipe collector 1360 when initially inserted into an ear canal. FIG. 11B schematically illustrates further insertion of the thin hollow pipe collector of FIG. 11A into the ear canal and collection of cerumen. Collector 1362 is attached to a, preferably, flexible shaft 1370 with a flexible section 1372. In this embodiment, the elastic foil 1362 includes gaps 1364. Gaps 1364 may be adapted to fine-tune the flexibility of elastic foil 1362 by being of varying sizes and/or shapes. Thus, a single thickness of foil may be used for car canals of different sizes, for non-limiting example, for adults and for children.

The flexible section, by enabling bending in all three dimensions, prevents resistance of the shaft to bending, especially about its longitudinal axis, and ensures that the longitudinal axis of the foil's distal end conforms to the tortuosity of the ear canal.

In the embodiment shown in FIGS. 11A and 11B, the flexible section 1372 includes accordion pleating. The flexible section 1372 in the shaft, by enabling bending in all three dimensions, increases the flexibility of the collector head while within the ear canal, prevents resistance of the shaft to bending, especially about its longitudinal axis, and directs the head towards the cerumen, by providing sufficient flexibility to the shaft in all three dimensions that the foil is in the same orientation as the cerumen.

The accordion pleating can be in the form of a plurality of substantially straight, substantially parallel rows, can be in the form of a continuous helix, or any combination thereof, so that the accordion pleating allows the shaft to bend in all three dimensions.

In other embodiments (described hereinafter), the flexible section can include a helical spring, a more flexible material, a plurality of thin regions hingedly connecting stiffer regions, a plurality of regions comprised of a more flexible material hingedly connecting stiffer regions, or any combination thereof.

FIG. 11C illustrates a front view of a deformable ring 1366 in its compressed state. Deformable ring 1366 may be located at the leading or distal end of thin hollow pipe collector 1360. Deformable ring 1366 may plastically deform if compressed sufficiently and, in use, may deform at approximately the point where the leading (distal) end of thin hollow pipe collector 1360 reaches its maximum depth within the ear canal.

In FIGS. 11A and 11B, the thin foil 1362 includes substantially the frustum of a cone, open at one edge to allow the cone to easily change its diameter and cone angle to match those of the ear canal, where the narrow end of the cone (at the right in FIGS. 11A and 11B) forms the leading (distal) edge and is deeper in the car canal than the wide (proximal) end of the cone (at the left in FIGS. 11A and 1B).

In some embodiments, the elastic foil includes, on its inner side, protrusions (not shown) adapted to collect the cerumen and guide the cerumen in the foil proximally, toward the shaft 1370, thereby clearing the distal portion of the elastic foil and allowing the elastic foil to collect further cerumen.

The height of the protrusions varies, starting from zero at their distal end and increasing towards their proximal end. In preferred embodiments, the height of the protrusions is a maximum near their proximal end, so that the protrusions collect the cerumen but do not push it, thereby preventing the device from forcing the cerumen deeper into the ear canal.

In preferred embodiments, the protrusions form at least the segment of a helix, the helix wrapping around the side of the frustum of the cone.

The protrusions can, in addition to guiding the cerumen, also function as struts to stiffen the elastic foil.

Figure 12:
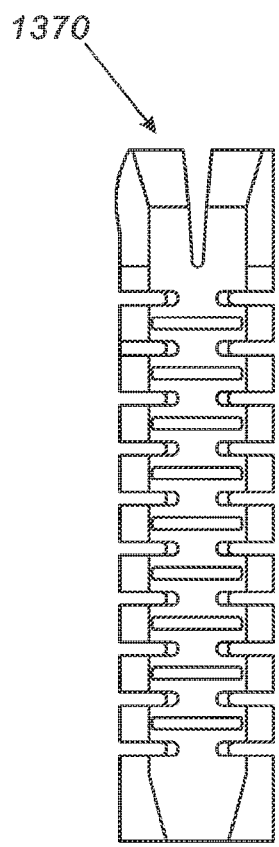
FIG. 12 schematically illustrates a shaft for a collector head.

FIG. 12 illustrates another embodiment of a shaft 1370 to hold the elastic foil collector head and direct it to the cerumen site. One of the main obstacles to inserting instruments into the ear canal is the tortuous shape of the canal and thus the high chance of injuring the ear canal wall during entry. In order to prevent pain and/or injury, the shaft is designed to bend in all three axes to follow the ear canal whenever it encounters a bend in any of the three dimensional directions.

Example 6

Figure 13:
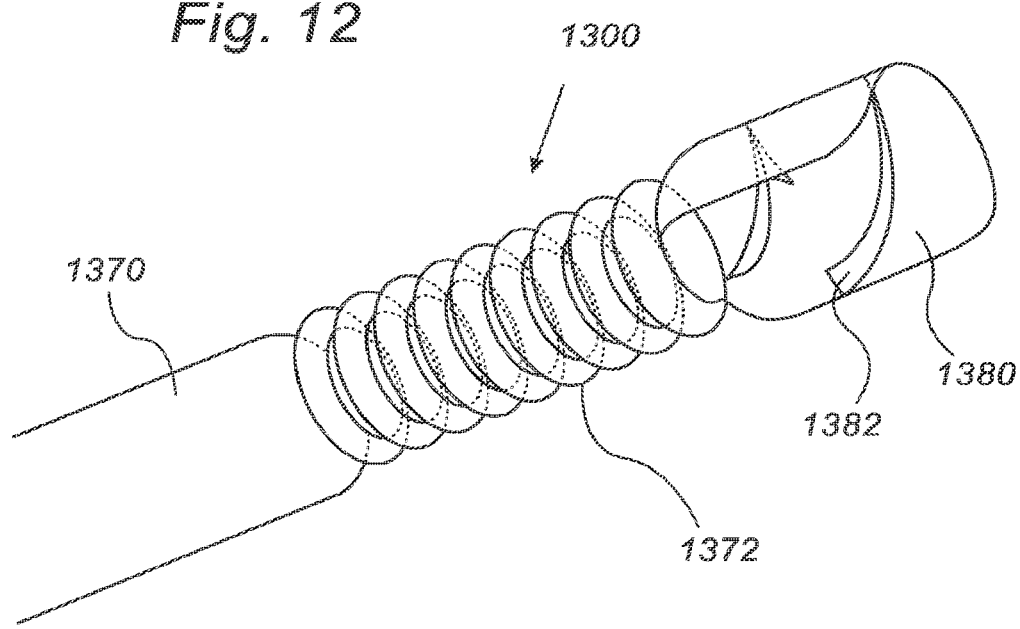
FIGS. 13-14 schematically illustrate embodiments of the collector head.

FIG. 13 illustrates an embodiment of a collector 1300 with a scoop head 1380. The embodiment includes a, preferably, flexible shaft 1370, a flexible section 1372 comprising, in this embodiment, accordion pleating, to provide flexibility, and a collector head 1380 shaped substantially like a scoop with a transverse cross-section which forms a segment of a circle, in this embodiment, approximately a half-circle. As the collector rotates, the sides of the collector head 1380 will scrape at or near the wall of the ear canal, thereby collecting the cerumen within the scoop 1380.

The material of the scoop is of a spring-like elastic material, such that the scoop, especially the edges thereof, is gently pressed against the walls of the ear canal. This ensures that the scoop passes between the cerumen and the walls of the ear canal, facilitating collection of the cerumen and preventing the scoop from pushing the cerumen deeper into the ear canal.

The flexible section, by enabling bending in all three dimensions, prevents resistance of the collector head to bending, especially about its longitudinal axis and ensures that the collector conforms to the tortuosity of the ear canal along its entire length.

The accordion pleating can be in the form of a plurality of substantially straight, substantially parallel rows, it can be in the form of a continuous helix, or any combination thereof, so that the accordion pleating allows the shaft to bend in all three dimensions.

In other embodiments (described hereinafter, the flexible section can include a helical spring, a more flexible material, a plurality of thin regions hingedly connecting stiffer regions, a plurality of regions comprised of a more flexible material hingedly connecting stiffer regions, or any combination thereof.

In some embodiments, the scoop head also includes at least one vane 1382 to collect the cerumen and guide the cerumen in the scoop proximally, toward the shaft 1370, thereby clearing the distal portion of the scoop and allowing the scoop to collect further cerumen. The embodiment shown includes two such vanes.

The height of the vanes varies, starting from zero at the vanes' distal end and increasing towards the vanes' proximal end. In preferred embodiments, the height of the vanes is a maximum near their proximal end, so that the vanes collect the cerumen but do not push it, thereby preventing the device from forcing the cerumen deeper into the ear canal.

In another variant of the scoop head collector, the means of guiding the cerumen to move proximally is at least one ridge. In all variants, the collection/guidance means varies in height from 0 at the distal end to a maximum near the proximal end.

Figure 14:
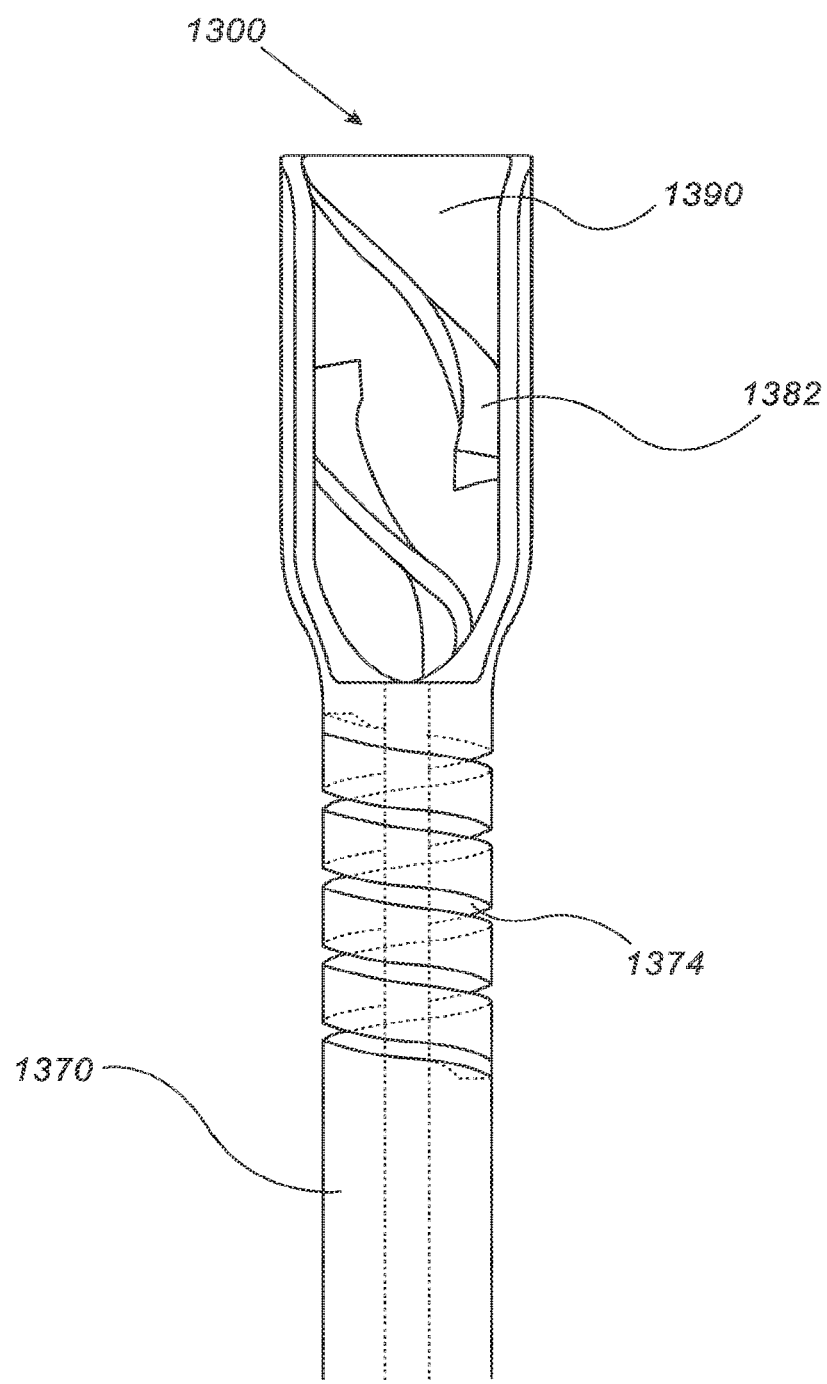

The vanes or ridges preferably form segments of a helix around the inside of the collector head. Helical vanes or ridges may be arranged such that the distal ends of the helices are separated longitudinally, as shown in FIG. 14. As another example, they may be separated transversely, for non-limiting example, such that two helices both end at the distal end of the collector, and any combination thereof.

In some embodiments, the scoop has no vanes or ridges. In some embodiments, the vanes or ridges are not helical, but are straight or circular within the collector head.

Example 7

FIG. 14 illustrates an embodiment of a shovel collector 1300 with a shovel head 1390. The embodiment includes a, preferably, flexible shaft 1370, a flexible section 1374 to provide flexibility and a collector head 1390 shaped substantially like a shovel with a transverse cross-section that is substantially U-shaped, being slightly curved in its center, with curved, nearly vertical sides. As the collector rotates, the sides of the collector head 1390 will scrape at or near the wall of the ear canal, thereby collecting the cerumen within the shovel 1390.

The material of the shovel is of a spring-like elastic material, such that the shovel especially the edges thereof, is gently pressed against the walls of the ear canal. This ensures that the shovel passes between the cerumen and the walls of the ear canal, facilitating collection of the cerumen and preventing the shovel from pushing the cerumen deeper into the car canal.

The flexible section, by enabling bending in all three dimensions, prevents resistance of the collector head to bending, especially about its longitudinal axis and ensures that the collector conforms to the tortuosity of the ear canal along its entire length.

The flexible section can include accordion pleating, a helical spring, a more flexible material, a plurality of thin regions hingedly connecting stiffer regions, a plurality of regions comprised of a more flexible material hingedly connecting stiffer regions, and any combination thereof.

The accordion pleating can be in the form of a plurality of substantially straight, substantially parallel rows, it can be in the form of a continuous helix, or any combination thereof, so that the accordion pleating allows the shaft to bend in all three dimensions.

In preferred embodiments, the scoop head also includes at least one vane 1382 to collect the cerumen and guide the cerumen in the shovel proximally, toward the shaft 1370, thereby clearing the distal portion of the shovel and allowing the shovel to collect further cerumen. The embodiment shown includes two such vanes.

The height of the vanes varies, starting from zero at the vanes' distal end and increasing towards the vanes' proximal end. In preferred embodiments, the height of the vanes is a maximum near their proximal end, so that the vanes collect the cerumen but do not push it, thereby preventing the device from forcing the cerumen deeper into the car canal.

In another variant of the shovel head collector, the means of guiding the cerumen to move proximally is at least one ridge.

In all variants, the collection/guidance means varies in height from 0 at the distal end to a maximum near the proximal end.

The vanes or ridges preferably form segments of a helix around the inside of the collector head. Helical vanes or ridges can be arranged such that the distal ends of the helices are separated longitudinally, as shown in FIG. 14, they can be separated transversely, for non-limiting example, such that two helices both end at the distal end of the collector, and any combination thereof.

In some embodiments, the shovel has no vanes or ridges. In some embodiments, the vanes or ridges are not helical, but are straight or circular within the collector head.

In the embodiment shown, the flexible section 1374 is in the form of a helical strip. Alternatively or in addition, the flexible section may include accordion pleating 1372 or a helical spring, may be segmented and connected by hinging sections, or any combination thereof. Other means of providing flexible connections, as is known in the art, may be used.

Preferred embodiments of collector heads designs such as the scoop or shovel or variants thereof include between ¼ and ½ of a cylinder, preferably about ⅓ of a cylinder.

Example 8

In accordance with an embodiment of the present invention, a cerumen removal device may include a collector head substantially in the general form of a helical spring. The collector head may be extended, without any surrounding sheath or housing, into the ear canal. The helical spring form has a substantially triangular cross section. Thus, a surface of the collector head that faces radially outward, toward the interior wall of the ear canal, is substantially flat. The surface of the collector head that faces radially inward, toward a longitudinal axis of the collector head, tapers to a blade-like edge.

Rotation of the collector head may collect earwax from within the ear canal (e.g., after, or concurrent with, introduction of a cerumen softening fluid into the ear canal). A flexible section or neck may enable the collector head to bend with respect to a longitudinal axis of a shaft that includes the collector head. Thus, when the collector head is inserted into the ear canal the collector head may align itself with a local orientation of the ear canal.

Figure 15A:
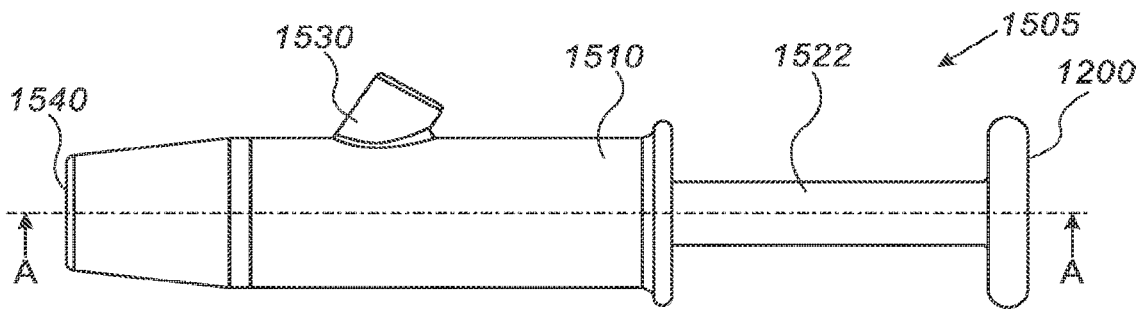
FIG. 15A shows an exterior view of a cerumen removal device with a helical spring earwax collector, in accordance with an embodiment of the present invention.
Figure 15B:
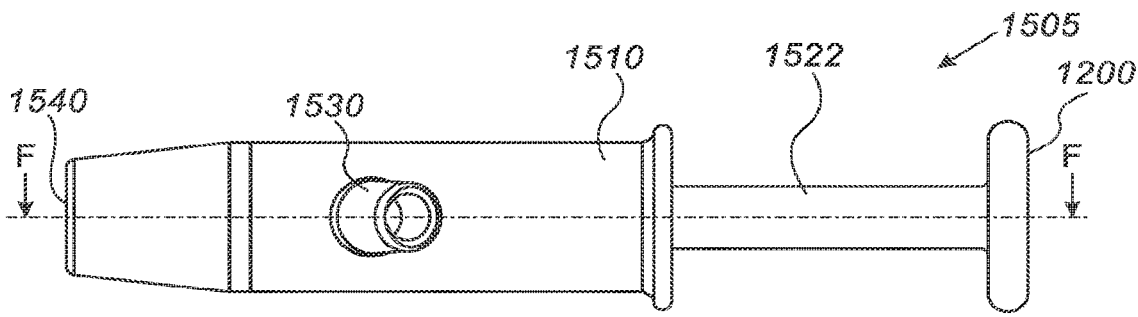
FIG. 15B shows a perpendicular exterior view of the device shown in FIG. 15A.
Figure 15C:
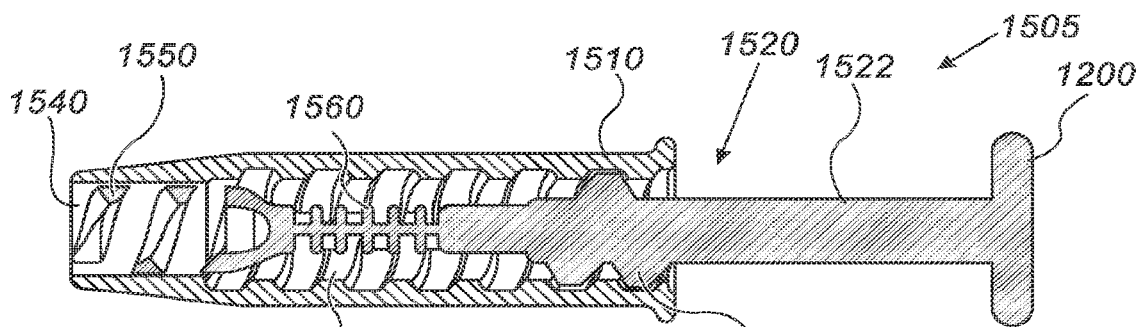
FIG. 15C shows cross section along plane AA of the device shown in FIG. 15A.
Figure 15D:
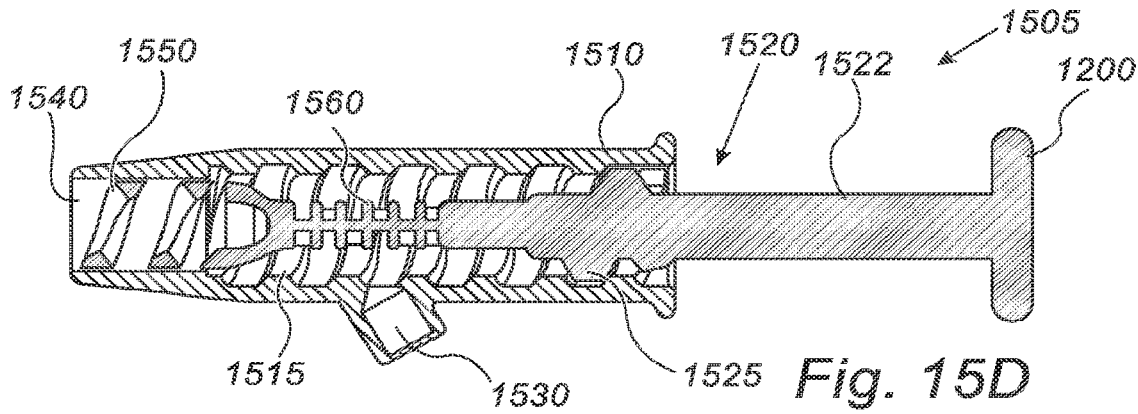
FIG. 15D shows cross section along plane FF of the device shown in FIG. 15B.

FIG. 15A shows an exterior view of a cerumen removal device with a helical earwax collector, in accordance with an embodiment of the present invention. FIG. 15B shows a perpendicular exterior view of the device shown in FIG. 15A. FIG. 15C shows a sectional view of the device shown in FIG. 15A along section AA. FIG. 15D shows a sectional view of the device shown in FIG. 15B along section FF.

Cerumen removal device 1505 incorporates helical collector head 1550 substantially in the form of a helix. Helical collector head 1550 is configured to extend out of cerumen removal device 1505 and into an ear canal to collect cerumen or earwax. Helical collector head 1550 is shaped in the form of a helical spring or helical strip that surrounds an elongated space within the helical strip. When extended out of cerumen removal device 1505, helical collector head 1550 is exposed, with no restricting structure surrounding helical collector head 1550. Thus, when helical collector head 1550 is inserted into a restrictive space, such as the ear canal, each part of helical collector head 1550 expands to fill the local cross section of the space (up to the unrestricted diameter of helical collector head 1550).

Cerumen removal device 1505 includes a housing in the form of device housing 1510 and a head assembly 1520 that includes knob 1200. Knob 1200 extends outward from device housing 1510. Device housing 1510 includes housing threading 1515 on its interior wall, while shaft 1522 of head assembly 1520 includes a corresponding cooperating shaft threading 1525. Thus, turning knob 1200 may screw head assembly 1520 into device housing 1510 to extend helical collector head 1550 out of head opening 1540. Head opening 1540 of device housing 1510 is distal to knob 1200 when cerumen removal device 1505 is assembled.

Cerumen removal device 1505 may include an inlet opening 1530 that is connectable to a source (e.g., bottle, vial, syringe, tap, or other source) of cerumen softening fluid. In some embodiments, inlet opening 1530 incorporates, or is permanently attached to, a reservoir of cerumen softening fluid. The cerumen softening fluid may be introduced into the ear canal prior to, concurrently with, or after insertion of helical collector head 1550 into the ear canal.

Knob 1200 is connected via shaft 1522 and flexible section 1560 to helical collector head 1550 to form head assembly 1520. Thus, rotating knob 1200 about its axis similarly rotates helical collector head 1550. Head opening 1540 may be placed at the exterior opening to the ear canal at the outer ear. Rotation of helical collector head 1550, together with engagement of shaft threading 1525 on knob 1200 with housing threading 1515 of device housing 1510, causes helical collector head 1550 to extend from head opening 1540 and into the ear canal.

Figure 16A:
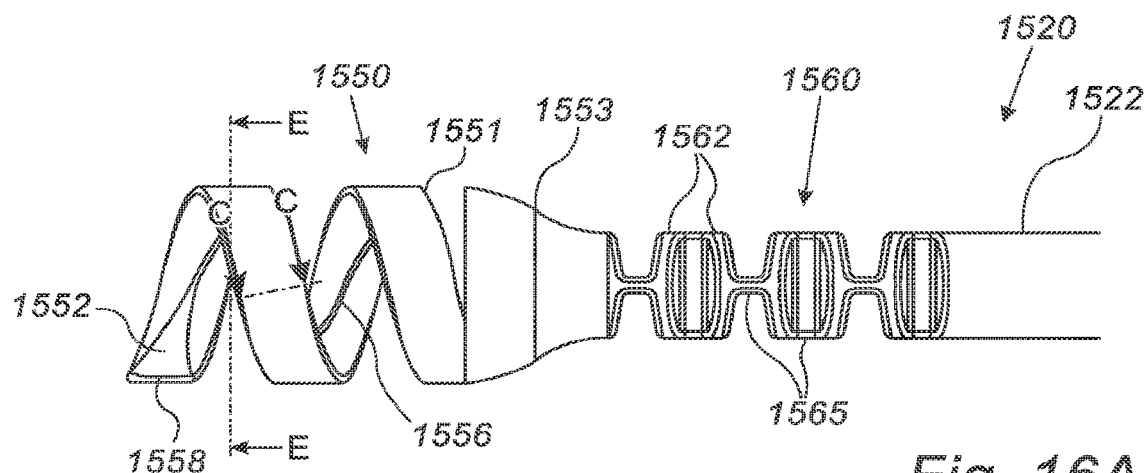
FIG. 16A shows details of a shaft of the device shown in FIG. 15A.

Flexible section 1560 may laterally bend in two dimensions perpendicular to the longitudinal axis of shaft 1522 or head assembly 1520. For example (e.g., as shown in FIG. 16A), lateral bending in the two dimensions may be enabled by alternating flexing sections, each bendable in a single dimension about an axis that is perpendicular to the longitudinal axis of head assembly 1520 and of flexible section 1560. The axes of bending of the alternating sections may be mutually perpendicular (e.g., when the longitudinal axis is labeled as an x-axis, the axes of bending may labeled as y- and z-axes). When helical collector head 1550 is inserted into the ear canal, the two-dimensional bending of flexible section 1560 may enable the longitudinal axis of helical collector head 1550 to remain substantially parallel to the longitudinal axis of the ear canal at any location along the path of the ear canal. Thus, helical collector head 1550 may approach cerumen in the ear canal with an orientation that may be optimal for collection the cerumen (while avoiding pushing the cerumen deeper into the ear canal). Furthermore, bending or deformation of helical collector head 1550 may be avoided or reduced when following the tortuosity of the ear canal. Thus, pressure or force exerted by helical collector head 1550 on the ear canal may be reduced or eliminated, thus avoiding pain. Remaining parallel to the ear canal may also eliminate or reduce the likelihood that the tip of helical collector head 1550 will poke the wall of the ear canal. Thus, the rotation of head assembly 1520 may both extend helical collector head 1550 into the ear canal and collect cerumen from within the ear canal. When cerumen is collected, helical collector head 1550 may be pulled out of the ear canal.

Since helical collector head 1550 has a spring-like structure, the diameter of helical collector head 1550 is not fixed and may vary along its length. Thus, the outer diameter of helical collector head 1550 may adapt automatically to match and fill the varying diameter of the ear canal. For example, the ear canal is narrower at the eardrum (internal) than at its opening at the outer ear. This narrowing of the ear canal is not uniform. The diameter of helical collector head 1550 may automatically self-adjust so that the outer diameter of helical collector head 1550 substantially matches the diameter of the ear canal at each point. Since the spring-like structure is resilient and is essentially free-standing, its diameter may adapt locally, further enabling the diameter spring-like structure to match that of the ear canal.

Helical collector head 1550 may be made of a flexible, resilient material. Suitable materials may include, but are not limited to, metal, polypropylene, high density or low density polyethylene polycarbonate, nylon, glass fiber, epoxy resin, carbon fiber, polyethylenimine (PEI), or any combination thereof.

Figure 16B:
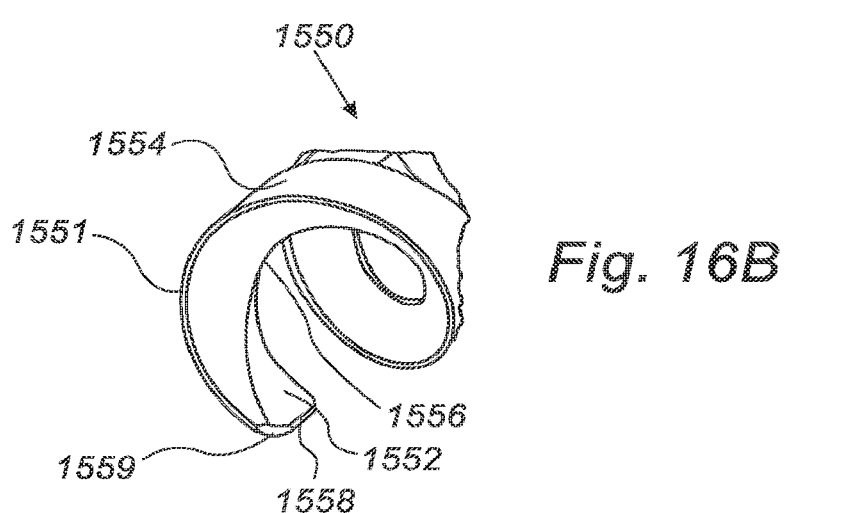
FIG. 16B shows the tip of a collector head of the shaft shown in FIG. 16A.
Figure 16C:
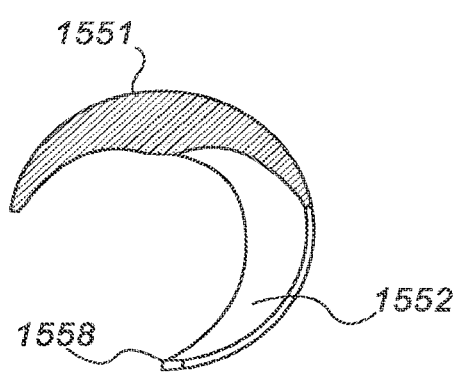
FIG. 16C shows a cut along plane EE of FIG. 16A.
Figure 16D:
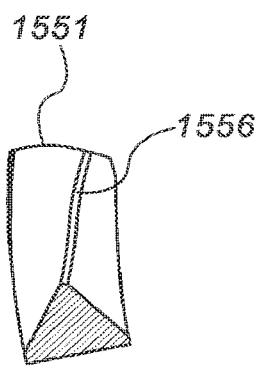
FIG. 16D shows a cut along plane CC of FIG. 16A.

FIG. 16A shows details of a helical collector head assembly, in accordance with an embodiment of the present invention. FIG. 16B shows the tip of a collector head of the collector head assembly shown in FIG. 16A. FIG. 16C shows a sectional view along section EE of FIG. 16A. FIG. 16D shows a sectional view along section CC of FIG. 16A.

Figure 17A:
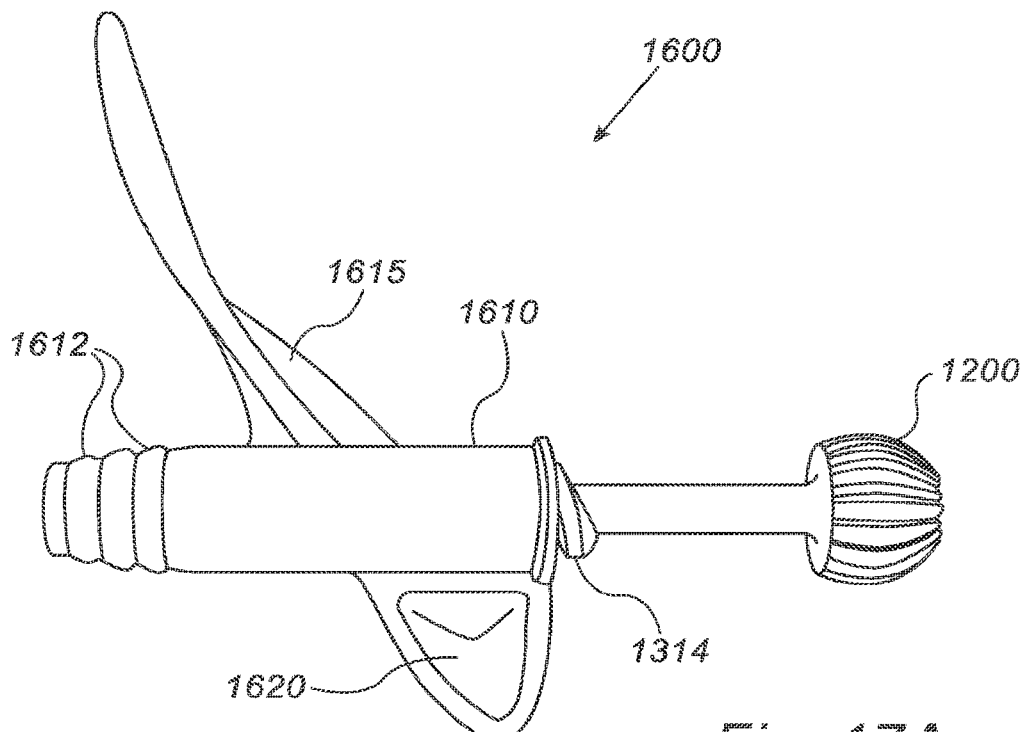
FIG. 17A shows a cerumen removal device with a helical spring earwax collector, in accordance with an embodiment of the present invention.

Head assembly 1520 may be used alone (e.g., by a healthcare professional who manually inserts helical collector head 1550 into the ear canal and manually manipulates shaft 1522 to remove earwax), or may be incorporated into a housing of a cerumen removal device, such as cerumen removal device 1505 (FIG. 15A) or 1600 (FIG. 17A). Shaft 1522 may include one or more markings. The markings may be indicative of a depth of helical collector head 1550 within the ear canal.

Helical strip 1551 of helical collector head 1550 surrounds an elongated and empty central space. A proximal end of helical strip 1551 may extend from a tapered section 1553.

Helical strip 1551 of helical collector head 1550 may have a substantially triangular, wedge-like, or radially inward-tapering cross section. Thus, outer surface 1554 of helical strip 1551 is substantially flat. The inward tapering, or apex of the triangle or wedge, points inward, forming interior edge 1556. The shape of interior edge 1556 may facilitate removal of earwax. For example, interior edge 1556 may hold collected earwax within helical collector head 1550 as helical collector head 1550 is removed from the ear canal.

A distal end of helical strip 1551 may taper to flatten to present a wedge 1552. Leading end 1558 of wedge 1552 may be substantially parallel to the axis of the helix as shown, or may be curved or form an oblique with respect to the axis. As used herein, a wedge refers to any structure that includes an end that tapers to a thin edge, whether or not the faces are flat (e.g., with a triangular profile) or curved (e.g., having a profile with a concave side).

The shape of wedge 1552 may facilitate insertion of helical collector head 1550 between a mass of earwax and the wall of the ear canal, or into a mass of earwax. The helical structure of helical collector head 1550 causes a local diameter along the length (longitudinal axis) of helical collector head 1550 to expand to match the local cross section of the ear canal (when the local cross section is smaller or equal to the natural unrestricted diameter of helical collector head 1550). Thus, the shape of wedge 1552 may facilitate separation of the cerumen (which may include hairs, dirt, detritus, or other inclusions) from the ear canal.

The distal end of wedge 1552 includes corners 1559 that are rounded or beveled. The rounded or beveled shape of corners 1559 may prevent poking, scratching, or injury to the ear canal.

The plane of section EE is perpendicular to the longitudinal axis of helical collector head 1550, while the plane of section CC is perpendicular to the spring-like structure of helical collector head 1550. Thus, the inward tapering cross-section of the spring-like structure of helical collector head 1550 is visible in FIG. 16D. FIG. 16C shows the transitioning to the inward tapering cross-section at the distal end of helical collector head 1550 to the flattened form of wedge 1552.

Thus, an outer surface of the collector head that faces radially outward, toward the interior wall of the ear canal, is substantially flat. The surface of the collector head that faces radially inward, toward a longitudinal axis of head assembly 1520, tapers to edge 1556. Edge 1556 may facilitate removal of collected cerumen from the ear canal.

Head assembly 1520 may be molded or otherwise manufactured in a single process. The composition of head assembly 1520 may include materials such as, for example, silicone, cellulose, polyurethane, high density or low density polyethylene (PE), polyamide, nylon, polyether ether ketone (PEEK), polyester silicone, polyester, polyvinyl chloride (PVC), polypropylene (PP), thermoplastics, elastomer, metal, another material or any combination thereof.

Flexible section 1560 is located adjacent to helical collector head 1550 at the distal end of shaft 1522 of head assembly 1520. Thus flexible section 1560 enables helical collector head 1550 to accurately conform to the orientation of a section of an ear canal into which helical collector head 1550 is inserted. For example, flexible section 1560 may include substantially rigid anchor segments 1562 (that substantially retain their shape when flexible section 1560 is bent) separated by flexible segments 1565.

In some cases, flexible segments 1565 may have the form of flat, thin connecting segments that are bendable, e.g., in a single lateral direction (about a single axis) in a hinge-like manner. The orientations of different flexible segments 1565 may differ from one another to allow bending about differently oriented axes (enabling lateral bending of flexible section 1560 within differently oriented planes, each plane orthogonal to an axis of bending). For example, alternating flexible segments 1565 may be oriented orthogonally to one another (but parallel to the longitudinal axis of head assembly 1520). Such a configuration may enable lateral bending in any direction that is orthogonal to the longitudinal axis. Anchor segments 1562 may be stiffer than flexible segments 1565. For example, anchor segments 1562 may have a disk-like or other flat shape, the plane of the shape being oriented substantially perpendicular to a longitudinal axis of head assembly 1520.

Alternatively or in addition, flexible section 1560 may include accordion pleating, a helix or helical spring, a flexible material (e.g., that is more flexible than the remainder of head assembly 1520), or another flexible arrangement. Accordion pleating may be in the form of a plurality of substantially straight, substantially parallel rows, in the form of a continuous helix, or any combination thereof, so that the accordion pleating allows the shaft to bend in any direction.

A helical spring may be incorporated within a flexible region of head assembly 1520, may be attached to the shaft (e.g., within its interior), or may be embedded within the shaft material. The spring may be made of metal, plastic, glass fiber, carbon fiber, or a combination thereof, or of any other suitable material as is known in the art. The plastic may include polycarbonate, plastic composites, Ultem® polyetherimide resin, or any other suitable plastic as is known in the art. When flexible section 1560 is not deformed (e.g., without being inserted into a bent section of the ear canal), the longitudinal axis of the helical spring is collinear with the longitudinal axis of head assembly 1520 and helical collector head 1550.

Head assembly 1520, or an earwax removal device that incorporates head assembly 1520, may be used without introduction of a cerumen dissolution agent into the ear canal. The construction of head assembly 1520 may enable removal of solidified cerumen. In some cases, an earwax removal device may be used after a cerumen-softening material or cerumen dissolution agent has been introduced into the ear canal. In such a case, the earwax removal device need not incorporate or be attachable to a reservoir of the cerumen-softening material. For example, such an earwax removal device may be employed 1 minute to 20 minutes after introduction of the cerumen-softening material. The cerumen-softening material may be introduced into the ear canal by a clinician or other healthcare professional, or by a nonprofessional user (e.g., a person from whose ear the earwax is to be removed, or another person) who may dispense a conventional cerumen-softening liquid from a bottle or vial into the ear. An earwax removal device that is configured for use by a nonprofessional may include a restraining structure to maintain a position of the device relative to the outer ear.

Figure 17B:
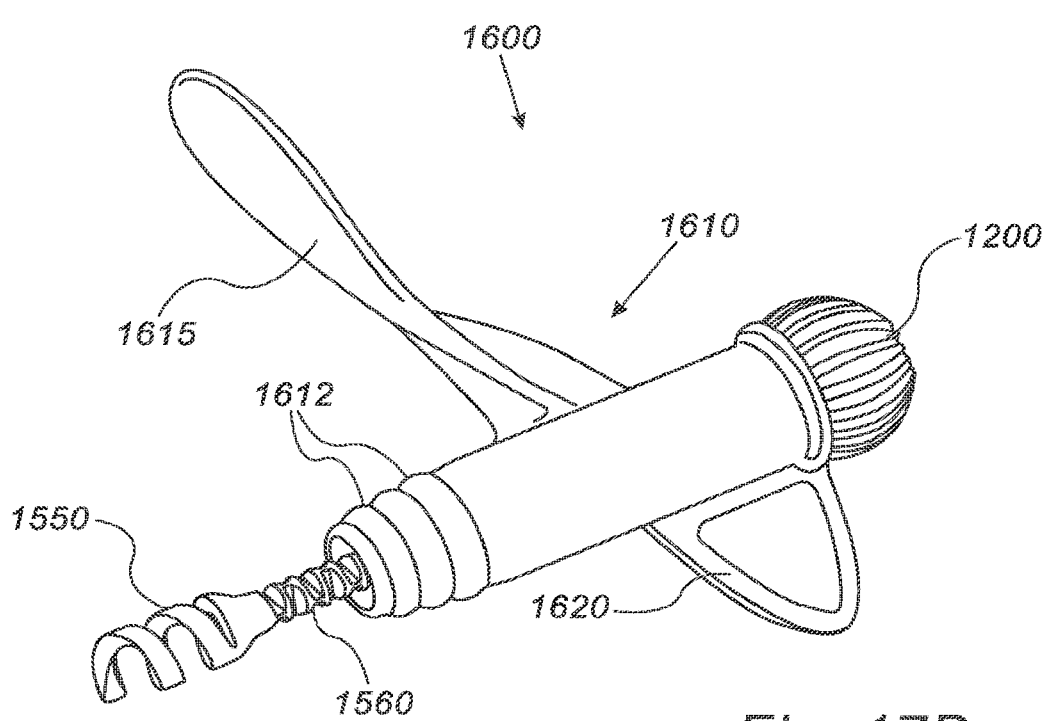
FIG. 17B shows the cerumen removal device of FIG. 17A with its collector extended.

FIG. 17A shows a cerumen removal device with a helical spring earwax collector, in accordance with an embodiment of the present invention. FIG. 17B shows the cerumen removal device of FIG. 17A with its collector extended. FIG. 17C is a sectional view showing internal components of the cerumen removal device shown in FIG. 17B.

Cerumen removal device 1600 may be configured for nonprofessional use (e.g., by a person from whose ear earwax is to be removed, or by another person without professional training with regard to earwax removal).

Cerumen removal device 1600 includes device housing 1610. A handle in the form of knob 1200 or another form extends outward from a proximal end of device housing 1610. When knob 1200 is rotated, the rotation causes extruding mechanism 1314 in the form of a screw structure (with threading on shaft 1522) to extend helical collector head 1550 outside of device housing 1610. Flexible section 1550 enables helical collector head 1550 to maintain a desired orientation within the ear canal during use.

Restrictor 1615 and fin 1620 are attached to device housing 1610. Restrictor 1615 and fin 1620 may have substantially flat wing-like structure. The outer contours of restrictor 1615 may be configured to match typical structure of the outer ear. Thus, restrictor 1615 may engage the outer car structure. Engaging the outer car may constrain an orientation of device housing 1610, e.g., such that helical collector head 1550 is extended approximately parallel to the ear canal at its exterior opening.

An end of device housing 1610 that includes head opening 1540 is provided with stopper structure 1612 in the form of a tapered plug. Stopper structure 1612 is configured to engage an exterior opening of the ear canal when head opening 1540 is placed within the ear canal. Engaging of the exterior opening of the ear canal may prevent insertion of helical collector head 1550 into the ear canal by more than a predetermined distance. For example, the predetermined distance may range from 10 mm to 20 mm, e.g., around mostly 15 mm, to ensure a clearance of at least 5 mm of helical collector head 1550 from the tympanic membrane (typically at a depth of 25 mm to 30 mm) when helical collector head 1550 is fully extended from head opening 1540. Stopper structure 1612 may include a tapering series of ring-like ridges of diameter that increases as the distance from head opening 1540 is increases. The tapering structure may ensure that stopper structure 1612 engages ear canal openings of different size.

When cerumen removal device 1600 is in use, restrictor 1615 may engage the outer ear of a person whose earwax is being removed. Engaging the outer ear may stabilize cerumen removal device 1600 when in use such that device housing 1610 maintains a desired orientation relative to the outer ear and the ear canal. The desired orientation may be in substantial alignment with the overall orientation of the ear canal. Thus, helical collector head 1550, as it is extended from device housing 1610, substantially aligned with the overall orientation of the ear canal at that point. Such an orientation may facilitate cerumen collection, eliminate or minimize pain, and prevent or reduce the likelihood of injury to the walls of the ear canal. Restrictor 1615, together with friction with stopper structure 1612, may also prevent rotation of device housing 1610 when knob 1200 is rotated. Device housing 1610 may be configured to maintain a safety distance between helical collector head 1550 and the eardrum by limiting restricting motion of knob 1200.

Fin 1620 may function as a graspable handle to enable a user to grasp or hold cerumen removal device 1600 during insertion of helical collector head 1550.

Figure 18:
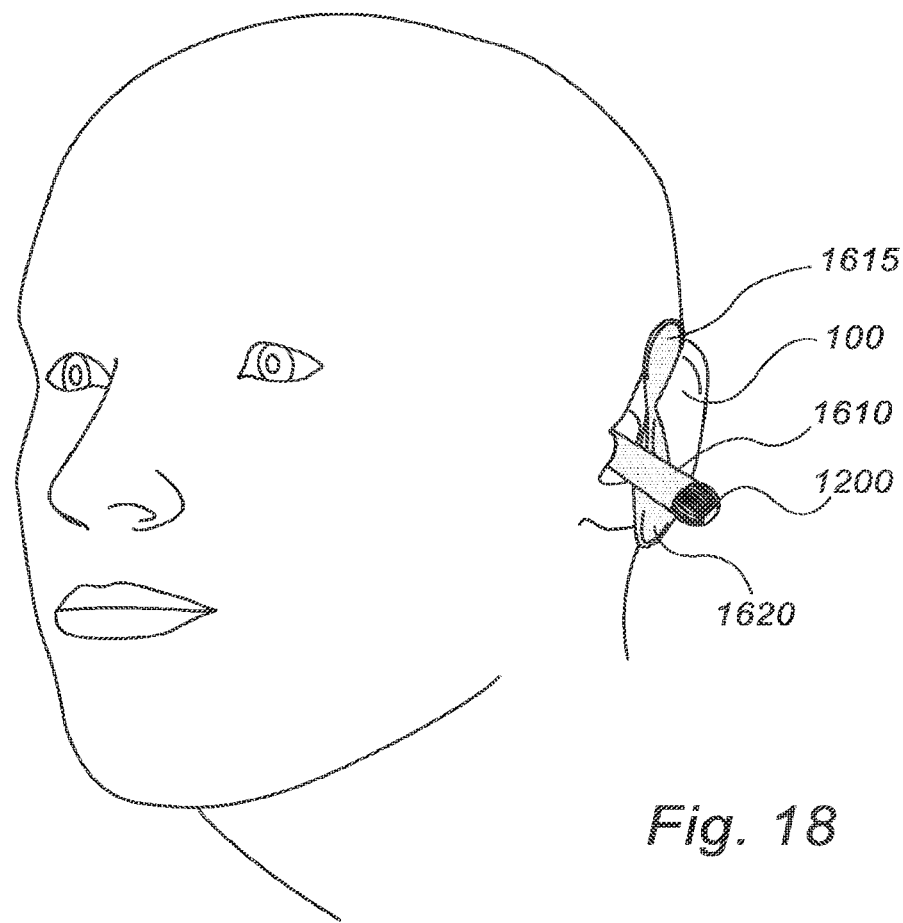
FIG. 18 schematically illustrates the cerumen removal device shown in FIG. 17A when inserted into an ear.

FIG. 18 schematically illustrates the cerumen removal device shown in FIG. 17A when inserted into an ear. Device housing 1610 is properly positioned when restrictor 1615 is resting against outer ear 100. When so positioned, fin 1620 may sit stably relative to the ear canal during use.

When head opening 1540 (FIG. 17C) of device housing 1610 is placed against the opening of the ear canal, a handle such as knob 1200 may be rotated (e.g., clockwise). A mechanism may be provided to ensure that knob 1200 is only rotatable in a single direction. For example, the mechanism may include a ratchet mechanism or other mechanism suitable for restricting a direction of rotation. Alternatively or in addition, device housing 1610 may include one or more markings to indicate a correct direction of rotation of knob 1200 or of shaft 1522.

Rotation of knob 1200 extends helical collector head 1550 out of head opening 1540 and into the ear canal. Continued rotation extends helical collector head 1550 to earwax within the ear canal. Continued rotation causes helical collector head 1550 to separate the earwax from the car canal and to collect the earwax (e.g., within, or between loops of, helical collector head 1550). When the earwax is collected, Knob 1200 or fin 1620 may be pulled outward to remove helical collector head 1550 with its collected earwax out of the ear canal. Device housing 1610 may be disposed of or emptied. Prior to, concurrent with, or following insertion of helical collector head 1550 into the ear canal, a cerumen softening fluid or cerumen dissolution agent may be introduced into the ear canal.

In accordance with an embodiment of the present invention, a tip of helical collector head 1550 that includes wedge 1552 (FIG. 16A) may be configured to adapt to a narrowing diameter within the ear canal or otherwise yield or bend to adapt to the car canal. Flexible section 1560 may be configured to bend gradually (e.g., to assume an arc-like form when bent, rather than bend at a single point), e.g., to enable a wider range of bending.

Figure 19:
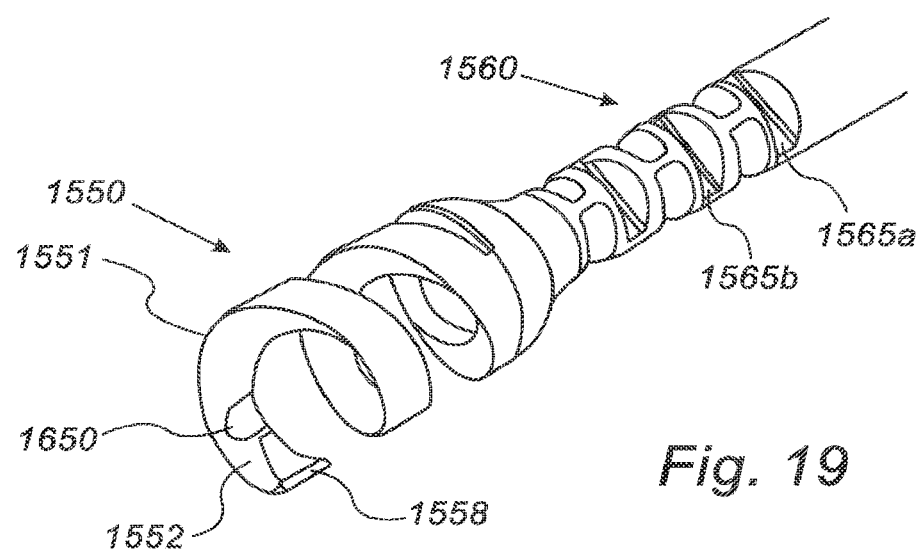
FIG. 19 shows a helical collector head with a bendable tip, in accordance with an embodiment of the present invention.

FIG. 19 shows a helical collector head with a bendable tip, in accordance with an embodiment of the present invention.

Helical collector head 1550 includes notch 1650. Notch 1650 enables wedge 1552 at a tip at a distal end of helical strip 1551 of helical collector head 1550 to bend (e.g., inward, toward the longitudinal axis of helical collector head 1550) relative to helical strip 1551. The bending of wedge 1552 may reduce or eliminate the possibility that leading end 1558 of wedge 1552 may scratch, poke, or injure the wall of the ear canal.

Flexible section 1560 may include flexible segments that differ from one another in their ability to bend (e.g., as measured by an elastic constant or modulus). For example, a thickness of flexible segment 1565a may differ from a thickness of flexible segment 1565b. For example, the thicknesses of the flexible segments may increase from one end of flexible section 1560 to the other (e.g., three segments with thicknesses of 0.50 mm, 0.55 mm, and 0.6 mm). For example, the thinnest segment may be adjacent to helical collector head 1550. The difference in thickness, or an otherwise achieved difference in flexibility (e.g., different materials or shaping of the surface), may ensure that more than one flexible segment of flexible section 1560 bends when flexible section 1560 is bent. Thus, the bending of flexible section 1560 may be gradual, with the entire length having a non-zero curvature (rather than a single flexible segment bending while the others remain substantially unbent).

The structure of wedge 1552 or notch 1650 may be designed such that wedge 1552 yields or bends when a bending force greater than a predetermined threshold force is exerted on wedge 1552. For example, one or more of a shape or size of notch 1650 (or one or more additional notches), a size and shape of wedge 1552, a selected material for construction of helical collector head 1550, may be selected or varied so as to yield to a particular value of the threshold bending force. The threshold bending force may be considered to be equivalent to the maximum lateral force that can be exerted by wedge 1552 on the wall of the ear canal. For example, a threshold bending force may be selected in accordance with known properties of the ear canal or of cerumen in the ear canal.

FIGS. 20A-20E show different configurations of a wedge and notch in substantially decreasing order of threshold bending force when constructed of a single material.

Figure 20A:
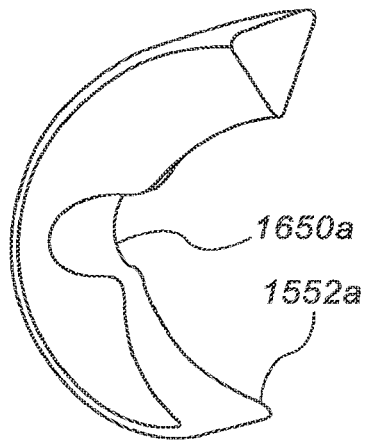
FIG. 20A shows a configuration of a distal end of helical collection head, in accordance with an embodiment of the present invention.

FIG. 20A shows a configuration of a distal end of helical collection head, in accordance with an embodiment of the present invention. Wedge 1552a and notch 1650a are configured for a threshold bending force that is greater than the threshold bending force of any of the configurations shown in FIGS. 20B-20E.

Figure 20B:
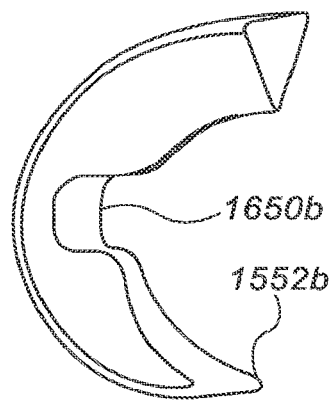
FIG. 20B shows a configuration of a distal end of helical collection head with a smaller threshold bending force than the configuration shown in FIG. 20A.

FIG. 20B shows a configuration of a distal end of helical collection head with a smaller threshold bending force than the configuration shown in FIG. 20A. The combination of wedge 1552b and notch 1650b is shaped to bend more easily than the combination of wedge 1552a and notch 1650a.

Figure 20C:
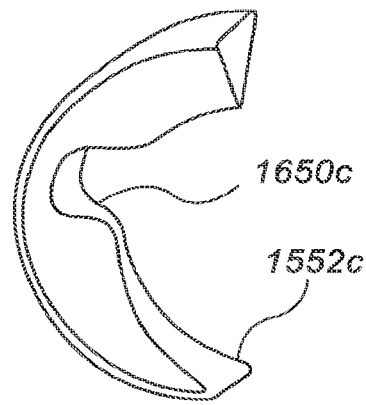
FIG. 20C shows a configuration of a distal end of helical collection head with a smaller threshold bending force than the configuration shown in FIG. 20B.

FIG. 20C shows a configuration of a distal end of helical collection head with a smaller threshold bending force than the configuration shown in FIG. 20B. The combination of wedge 1552c and notch 1650c is shaped to bend more easily than the combination of wedge 1552h and notch 1650b.

Figure 20D:
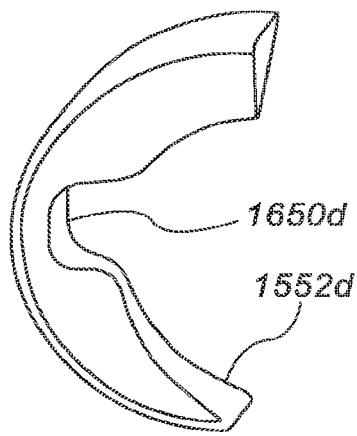
FIG. 20D shows a configuration of a distal end of helical collection head with a smaller threshold bending force than the configuration shown in FIG. 20C.

FIG. 20D shows a configuration of a distal end of helical collection head with a smaller threshold bending force than the configuration shown in FIG. 20C. The combination of wedge 1552d and notch 1650d is shaped to bend more easily than the combination of wedge 1552c and notch 1650c.

Figure 20E:
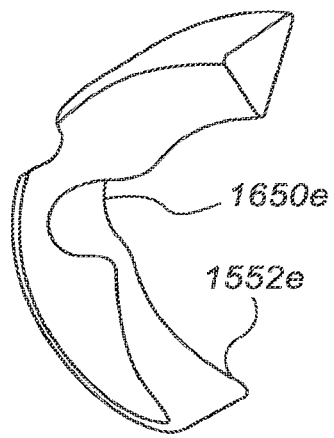
FIG. 20E shows a configuration of a distal end of helical collection head with a smaller threshold bending force than the configuration shown in FIG. 20D.

FIG. 20E shows a configuration of a distal end of helical collection head with a smaller threshold bending force than the configuration shown in FIG. 20D. The combination of wedge 1552c and notch 1650c (in this case a double notch) is shaped to bend more easily than the combination of wedge 1552d and notch 1650d.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A device for removing earwax from an ear canal, comprising:
  a shaft;
  an earwax collector head; and
  a flexible section between the earwax collector head and the shaft, wherein the earwax collector head is enclosed in a housing having an opening, wherein the housing is adapted to enable the earwax collector head to extend outwardly from the opening of the housing when the shaft is rotated; and
  wherein the earwax collector head includes a helical strip surrounding a substantially elongated space and ending with a strip distal end, wherein the strip distal end flattens to presents a blade-like end, allowing to amass said earwax into said space via said strip distal end, wherein the earwax collector head has a longitudinal axis, wherein the helical strip has an interior surface facing radially inward toward the longitudinal axis of the earwax collector head, wherein the interior surface of the helical strip tapers radially inwardly to a blade-like edge, wherein the blade-like edge removes at least a portion of the earwax from an ear canal when the shaft is rotated while the earwax collector head is inserted into the ear canal, and wherein the flexible section is designed to enable bending in all three dimensions and includes substantially rigid anchor segments separated by flexible segments.

2. The device of claim 1, wherein the earwax collector head is deformable, wherein the deformable earwax collector head is adapted to fit a size and a shape of the ear canal when the earwax collector head is inserted into the ear canal.

3. The device of claim 1, wherein the interior surface is adapted to hold collected earwax within the earwax collector head as the earwax collector head is removed from the ear canal.

4. The device of claim 1, wherein the earwax collector head has a local diameter along the longitudinal axis, wherein the local diameter adapts automatically to match and fill a varying diameter of the ear canal.

5. The device of claim 1, wherein the housing includes an inlet for connecting the earwax collector head to a source of a cerumen dissolution agent.

6. The device of claim 5, wherein the cerumen dissolution agent is configured to be introduced into the ear canal when the earwax collector head is inserted into the ear canal.

7. The device of claim 1, wherein the shaft includes a knob, wherein the knob limits the outward extension of the earwax collector head.

8. The device of claim 1, wherein the rigid anchor segments substantially retain their shape when the flexible section is bent.

9. A device for removing earwax from an ear canal, comprising:
- a shaft; and
- an earwax collector head including a helical strip surrounding a substantially elongated space and ending with a strip distal end, wherein the strip distal end flattens to present a blade-like end, the earwax collector head having a longitudinal axis, wherein the earwax collector head has an outer diameter along the longitudinal axis, wherein the outer diameter of the earwax collector head is adapted to vary along the longitudinal axis such that the outer diameter of the earwax collector head adjusts to a varying diameter of an ear canal when the earwax collector head is inserted into the ear canal, wherein the earwax collector head is connected to the shaft and enclosed in a housing having an opening configured to enable the earwax collector head to extend outward from the opening of the housing when the shaft is rotated, wherein the earwax is collected in the collector head when the earwax collector head is inserted into the ear canal and the shaft is rotated.

10. The device of claim 9, further comprising:
- a flexible section between the collector head and the shaft, wherein the flexible section is designed to enable bending in all three dimensions.

11. The device of claim 9, wherein the interior surface is adapted to hold collected earwax within the earwax collector head as the earwax collector head is removed from the ear canal.

12. The device of claim 9, wherein the housing includes an inlet for connecting the earwax collector head to a source of a cerumen dissolution agent.

13. The device of claim 12, wherein the cerumen dissolution agent is configured to be introduced into the ear canal when the earwax collector head is inserted into the ear canal.

14. The device of claim 9, wherein the shaft includes a knob, wherein the knob limits the outward extension of the earwax collector head.

15. The device of claim 9, wherein the blade-like end is substantially parallel to the longitudinal axis of the helical strip.

16. The device of claim 9, wherein the collector head comprises a notch to allow bending of the strip distal end upon a bending force exerted thereon.

17. The device of claim 9, wherein the blade-like end includes corners that are rounded or beveled.

* * * * *